(12) United States Patent
Fukiage et al.

(10) Patent No.: US 6,582,932 B1
(45) Date of Patent: Jun. 24, 2003

(54) CALPAIN AND DNA ENCODING THE SAME

(75) Inventors: Chiho Fukiage, Katano (JP); Mitsuyoshi Azuma, Nishinomiya (JP)

(73) Assignee: Senju Pharmaceutical Co., Ltd., Osaka (JP)

(*) Notice: Subject to any disclaimer, the term of this patent is extended or adjusted under 35 U.S.C. 154(b) by 0 days.

(21) Appl. No.: 09/622,880

(22) PCT Filed: Feb. 26, 1999

(86) PCT No.: PCT/JP99/00903

§ 371 (c)(1), (2), (4) Date: Aug. 24, 2000

(87) PCT Pub. No.: WO99/45107

PCT Pub. Date: Sep. 10, 1999

(30) Foreign Application Priority Data

Mar. 2, 1998 (JP) ............................................. 10-049430

(51) Int. Cl.$^7$ ......................... C12P 21/06; C07K 14/00; C07K 16/00
(52) U.S. Cl. ........................ 435/69.1; 530/326; 530/350
(58) Field of Search ...................... 435/6, 69.1; 514/44; 536/23.1, 24.3, 24.33, 24.31, 24.5, 24.1; 530/350, 387.1

(56) References Cited

FOREIGN PATENT DOCUMENTS

| EP | 0 717 110 | 6/1996 |
|---|---|---|
| WO | 96/16175 | 5/1996 |

OTHER PUBLICATIONS

H Ma et al.,IOVS, "Cloning and Expression of mRNA for Calpain Lp82 from Rat Lens:Splice Variant of p94," Feb. 1998, vol. 39, No. 2, pp. 454–460.*
H Ma et al., GenBank Accession No. U96367. Mar. 1998.*
Seikagaku (Biochemistry), vol. 65, pp. 537–552, 1993–together with an English translation of a pertinent part.
Jikken Igaku (Experimental Medicine), vol. 13, pp. 35–42, 1995–together with an English translation of a pertinent part.
Atarashii Ganak (Journal of the Eye), vol. 13, pp. 993–1001, 1996–together with an English translation of a pertinent part.
Atarashii Ganka (Journal of the Eye), vol. 12, pp. 239–250, 1995–together with an English translation of a pertinent part, and abstract of Nature 1990, Jan. 25:343 (related document).
H. Sorimachi et al., "Molecular Cloning of a Novel Mannalian Calcium–dependent Protease Distinct from Both m– and μ–types", The Journal of Biological Chemistry, vol. 264, No. 33, pp. 20106–20111, Nov. 25, 1989.
I. Richard et al., "Mutations in the Proteolytic Enzyme Calpain 3 Cause Limb–Girdle Muscular Dystrophy type 2A", Cell, vol. 81, pp. 27–40, Apr. 7, 1995.
I. Richard et al., "Molecular Cloning of Mouse Canpe3, the Gene Associated with Limb–Girdle Muscular Dystrophy 2A in Human", Mammalian Genome, vol. 7, pp. 377–379, 1996.
K. Wang et al., "Development and Therapeutic Potential of Calpain Inhibitors", Advances in Pharmacology, vol. 37, pp. 117–152, 1997.
L. David et al., "Purification of Calpain II from Rat Lens and Determination of Endogenous Substrates", Exp., Eye Research, vol. 42, pp. 227–238, 1986.
U.K. Laemmli, "Cleavage of Structural Proteins during the Assembly of the Head of Bacteriophage T4", Nature, vol. 227, pp. 680–685, 1970.
H. Towbin et al., "Electrophoretic Transfer of Proteins from Polyacrylamide Gels to Nitrocellulose Sheets: Procedure and some Applications", Proc. Natl. Acad. Sci., vol. 76, No. 9, pp. 4350–4354, Sep. 1979.
J. Biol. Chem., vol. 264, No. 33, 1989, Sorimachi H. et al., "Molecular cloning of a novel mammalian calcium–dependent prorease distinct from both m–and μ–types", pp. 20106–20111.
Cell, vol. 81, No. 5, 1995, Richard I. et al., "Mutations in the proteolytic enzyme calpain 3 cause limb–girdle muscular dystrophy type 2A", pp. 27–40.
Mamm. Genome, vol. 7, No. 5, 1996, Richard I. et al., "Molecular cloning o mouse canp3, the gene associated with limb–girdle muscular dystrphy 2A in human", pp. 377–379.
Biochim. Biophys. Acta, vol. 1261, No. 3, 1995, Sorimachi H. et al., "Identification of a third ubiquitous calpain species—chicken muscle expresses four distinct calpains", pp. 381–393.

* cited by examiner

*Primary Examiner*—Sean McGarry
*Assistant Examiner*—Janet L. Epps-Ford
(74) *Attorney, Agent, or Firm*—Wenderoth, Lind & Ponack, L.L.P.

(57) ABSTRACT

A calpain protein which is specific for the retina in eye tissues containing a protein having an amino acid sequence represented by SEQ ID NO: 1 in Sequence Listing; a DNA represented by SEQ ID NO: 2 in Sequence Listing which encodes the above protein; a vector containing this DNA; a transformant transformed by this vector; and a process for producing the calpain protein which comprises culturing the transformant.

5 Claims, 16 Drawing Sheets

Fig. 3
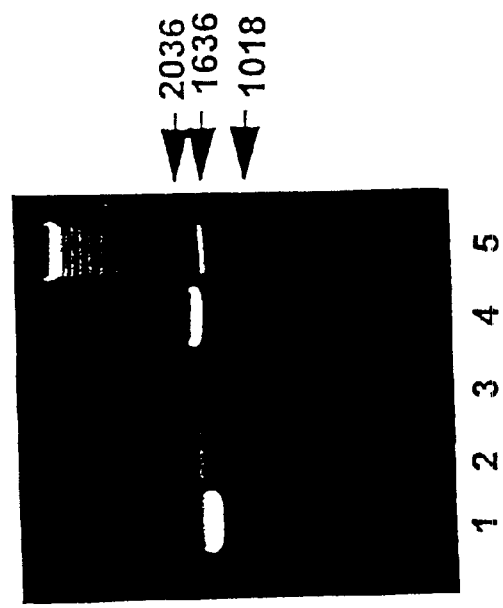
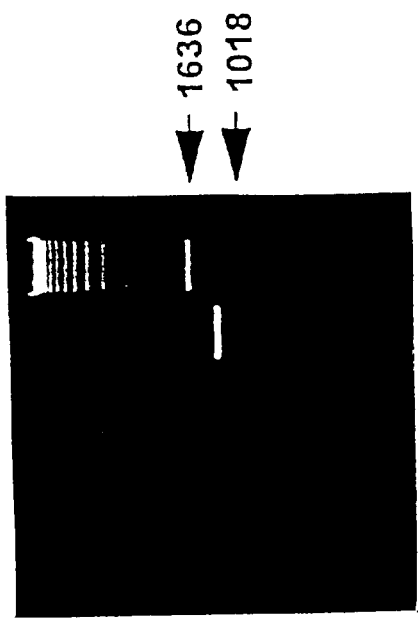

Fig. 5

```
p94    tttctttt tttcctctgg caagcctgct gctggtaggc accccaggt agaagctgcg tctaaatcct ttattgcctc ttcctcagga    89
p94    ataccattg ctctagggtc atagttcacc tatttaagct ggtcagagge cagccaattg tctgatagga tttaaactt gaagagactg tagccattt    189
p94    tttcctcaga tgacagaatc acttcaactt ccactttgta atgcttcct cttcttgaag gtagctgaat cttgttttct ttaaaaacgt cttccttcca    289
R188                                                            tcag gcctgggctg agggtgcagc aggagaggcc aggagaggag ccgggttcca ctgctcgtca tcATGCCCTA CCTGCTGCCG GGATTCTTCT    94
p94    aagttgcctg ccATGCCACTGA CGTTATTAGT CCAACTGTGG CCCCAAGGAC AGGACTGGAG CCCAGGTCCC CAGGGCCAGT TCCTCACCA GCTCAAGGCA    389
                 Start codon                                                            NS R188   GTGACAGAGT GATCAGAGAA AGGGACAGGA GAAATGGAGA GGGCCACCGTC TCAAGTTGA GGGGCAGGAT TTTGTCGTTC TCAAACAACG    194
p94    AGACCACTGA GGCTGGAAGT GGACCACCCG GTGGCATCTA TTCAGCCCCA ATTTTCCGAT CATTGGTGTG AAAGAGAGA CATTCGAGCA    489

R188   GTGTCTGGCT CAGAAGTGCC TCTTTGAAGA TCGAGTCTTC CCAGCAGGTA CACAGGCCCT TGGCTCACAT GAGCTGAGCC AGAAAGCCAA GATGAAGGCC    294
p94    GCTCCACAAG AAGTGCCTGG AGAGAAAGT TCTTTACCTG GATCCCGGA TCTTTTACA TCTTTTATCT CTCTTTACA TGAGACCTCT CTCTTTACA GCCAGAAGTT CCCCATCCAG    589
```

Fig. 6

|  | Exon1▼ |  |  |  |  |  |  |
|---|---|---|---|---|---|---|---|
| R188 | ATCACTTGGA | AGAGCCAAA | GGAGCCTT | GAGAATCCCC | GATTTATCAT | TGGTGGAGCC | ACAGGACTG | ACATCTGCCA | AGGAGATCTA | 394 |
| p94 | TTCGTCTCGGA | AGAGCTTCC | GGAGACCTCC | GGAGAATCCCC | GATTTATCAT | TGGTGGAGCC | ACAGGACTG | ACATCTGCCA | AGGAGATCTA | 689 |

Domain I ▼

Exon2 ▼
GGGACTGCT 394
GGGACTGCT 689

| R188 | GGTTTCTTGC | AGCCATTGCC | TGTCTGACCC | TGAATGAGCG | ACTGCTTTC | CGAGTTATAC | AAGTTTCACT | GAAAACTACG | CAGGGATCTT | 494 |
| p94 | GGCTTCTTGC | AGCCATTGCC | TGTCTGACCC | TGAATGAGCG | ACTGCTTTC | CGAGTTATAC | AAGTTTCACT | GAAAACTACG | CAGGGATCTT | 789 |

Exon3 ▼

| R188 | CCACTTCCAG | TTCTGGGCCT | ATGGAGACTG | GTTAGATGTG | ACTGCTCTGCC | GACATACAAC | AACCAGCTGG | TCTTCACCAA | ATCCAACCAC | 594 |
| p94 | CCACTTCCAG | TTCTGGGCCT | ATGGAGACTG | GTTAGATGTG | ACTGCTCTGCC | GACATACAAC | AACCAGCTGG | TCTTCACCAA | ATCCAACCAC | 889 |

Exon4 ▼

| R188 | CGGAATGAGT | TCTGGAGTGC | CCAATCATATG | CCAACTCCA | AAAGCATATG | TCTACTGGAG | GAAGCTCTGA | AAGTGGGAA | CACCACAGAA | GCCATGGAGG | 694 |
| p94 | CGCAATGAGT | TCTGGAGTGC | CCAATCATATG | CCAAGCTCCA | AAAGCATATG | TCTACTGGAG | GAAGCTCTGA | AAGTGGGAA | CACCACAGAA | GCCATGGAGG | 989 |

| R188 | ACTTCACAGG | AGGGTGACA | GAGTTTTTG | AGATCAAGGA | TGCTCCGAGT | GACATGTACA | AGATCATGAG | GAAAGCTATC | GAGAGAGGCT | CCCTCATGGG | 794 |
| p94 | ACTTCACAGG | AGGGTGACA | GAGTTTTTG | AGATCAAGGA | TGCTCCGAGT | GACATGTACA | AGATCATGAG | GAAAGCTATC | GAGAGAGGCT | CCCTCATGGG | 1089 |

Fig. 7

| | | | | | | |
|---|---|---|---|---|---|---|
| Rt88 | CTGCTCCATT | GATGATGGCA | CCAACATGAC | TTATGGAACC | TCTCCTTCTG | GTCTGAACAT | GGGGAATTG | ATTGCGCGGA | TGGTGAGAAA | TATGGATAAC | 894 |
| p94 | CTGCTCCATT | GATGATGGCA | CCAACATGAC | TTATGGAACC | TCTCCTTCTG | GTCTGAACAT | GGGGAATTG | ATTGCGCGGA | TGGTGAGAAA | TATGGATAAC | 1189 |

▲ Exon5                                                                                    IS1

| Rt88 | TGGCTGCTCA | GAGACTCAGA | CCTGGACCCC | AGGGCCTCAG | ATGACAGACA | GTCACGGACA | ATTGTTCCGG | TGCAGTATGA | AACAAGAATG | GCCTGTGTGGAC | 994 |
| p94 | TGGCTGCTCA | GAGACTCAGA | CCTGGACCCC | AGGGCCTCAG | ATGACAGACA | GTCACGGACA | ATTGTTCCGG | TGCAGTATGA | AACAAGAATG | GCCTGTGTGGAC | 1289 |

▲ Exon6

| Rt88 | TGGTGAAAGG | GCAGCCTAT | TCAGTCACTG | GGCTGGAGGA | GGCCCTGTTC | AAAGGCGAGA | AGTTGAAGCT | GGTGCGGCTG | CGGAACCCCT | GGGGCCAGT | 1094 |
| p94 | TGGTGAAAGG | GCAGCCTAT | TCAGTCACTG | GGCTGGAGGA | GGCCCTGTTC | AAAGGCGAGA | AGTTGAAGCT | GGTGCGGCTG | CGGAACCCCT | GGGGCCAGT | 1389 |

▲ Exon7

| Rt88 | GGAGTGGAAC | GGCTCTTGA | GTGATGGTTG | GAAGGACTGG | AGCTTTGTGTG | ACAAAGACGA | GAAGGCCCGT | CTGCAGCCC | AGGTCACGGA | GGATGGAGAG | 1194 |
| p94 | GGAGTGGAAC | GGCTCTTGGA | GTGATGGTTG | GAAGGACTGG | AGCTTTGTGTG | ACAAAGACGA | GAAGGCCCGT | CTGCAGCCCC | AGGTCACGGA | GGATGGAGAG | 1489 |

▲ Exon8

| Rt88 | TTCTGGATGT | CATATGATGA | CTTTTGTCTAC | CATTTCACAA | AGCTGGAGAT | CTGCAACCTC | ACAGCTGATG | CCCTGGAGTC | CGATAAGCTT | CAGACCTGA | 1294 |
| p94 | TTCTGGATGT | CATATGATGA | CTTTTGTCTAC | CATTTCACAA | AGCTGGAGAT | CTGCAACCTC | ACAGCTGATG | CCCTGGAGTC | CGATAAGCTT | CAGACCTGA | 1589 |

▲ Exon9

Domain II →

Fig. 8

|  |  |  |  |  |  |  |
|---|---|---|---|---|---|---|
| Rt88 | CAGTGTCTGT | AAATGAGGGC | CGCTGGGTGA | GGGGCTGTTC | TGCTGGAGGC | TGCGGAACT | TCCCAGACAC | TTTCTGGACC | AACCGGAGT | ACGGTCTCAA | 1394 |
| p94  | CAGTGTCTGT | AAATGAGGGC | CGCTGGGTGA | GGGGCTGTTC | TGCTGGAGGC | TGCGGAACT | TCCCAGACAC | TTTCTGGACC | AACCGGAGT | ACGGTCTCAA | 1689 |

▶ Exon10

| Rt88 | GCTCCTGGAG | GAGGATGATG | ACCCTGATGA | CTCTGAGGTG | ATTTGCAGT | TCCTGGTGGC | TCTGATGCAG | AAAAATCGGC | GCAAGGACCG | GAAGCTGGGG | 1494 |
| p94  | GCTCCTGGAG | GAGGATGATG | ACCCTGATGA | CTCTGAGGTG | ATTTGCAGT | TCCTGGTGGC | TCTGATGCAG | AAAAATCGGC | GCAAGGACCG | GAAGCTGGGG | 1789 |

▶ Exon11 ▶ Exon12

| Rt88 | GCCAACCTCT | TCACCATTGG | CTTCGCTATC | TAGGAGTTC | CCAAGAGAT | GCAGGGAAT | AAGCAACACC | TGCAGAAGA | CTTCTCTCTG | TACAATGCCT | 1594 |
| p94  | GCCAACCTCT | TCACCATTGG | CTTCGCTATC | TAGGAGTTC | CCAAGAGAT | GCAGGGAAT | AAGCAACACC | TGCAGAAGA | CTTCTCTCTG | TACAATGCCT | 1889 |

| Rt88 | CCAAGGCCAG | GAGCAAAACC | TACATCAACA | TGGGGGAGGT | GTCCAGAGCC | TTCGCCTGC | CGCCCAGGA | GTATGTCATT | GTCCCCTCCA | CTTACGAGCC | 1694 |
| p94  | CCAAGGCCAG | GAGCAAAACC | TACATCAACA | TGGGGGAGGT | GTCCAGAGCC | TTCGCCTGC | CGCCCAGGA | GTATGTCATT | GTCCCCTCCA | CTTACGAGCC | 1989 |

▶ Exon13 ▶ Exon14

| Rt88 | CCATCAGGAG | GGGGAATTCA | TCCTCGGGGT | CTTCTCTGAA | AAGAGGAATC | TCTCTGAGGA | AGCTGAGAAT | ACAATCTCTG | TGGACGGGCC | AGTG—— | 1788 |
| p94  | CCATCAGGAG | GGGGAATTCA | TCCTCGGGGT | CTTCTCTGAA | AAGAGGAATC | TCTCTGAGGA | AGCTGAGAAT | ACAATCTCTG | TGGACGGGCC | AGTGAAAAG | 2089 |

```
                                                                                                    Exon21 ▼
R188  TCTTCAAACA CTATGACACT GACCATTCTG GTACCATCAA TACTCATGAG ATGGGAAATG CAGTCAATGA TGCAGGCTTC CATCTCAACA GCCAACTCTA  2162
p94   TCTTCAAACA CTATGACACT GACCATTCTG GTACCATCAA TACTCATGAG ATGGGAAATG CAGTCAATGA TGCAGGCTTC CATCTCAACA GCCAACTCTA  2589

Exon22 ▼
R188  TGCATCATC ACCATGGCT AGGCAGACAA ACACATTCAT ATGACTTCAT CTGCTGCTTC GTCAGGCTGG AAGGGATGTT CAGAGCTTTT  2262
p94   TGCATCATC ACCATGGCT AGGCAGACAA ACACATTCAT ATGACTTCAT CTGCTGCTTC GTCAGGCTGG AAGGGATGTT CAGAGCTTTT  2689

Exon23 ▼
R188  CAGGCATTTG ACAAGGATGG AGATGGCATC ATCAACACTGA AGTACTTGA AGTACTTGAC GTGGCTGCAG GTGGCTGCCAG CTTACCATGT ATGCCTGAac  cagatgacct  2353
p94   CAGGCATTTG ACAAGGATGG AGATGGCATC ATCAACACTGA AGTACTTGA AGTACTTGAC GTGGCTGCAG GTGGCTGCCAG CTTACCATGT ATGCCTGAac  cagatgacct catgtaagat  2789
                                                                                              Domain IV  Stop codon p94   caaccaggat tccatctcaa cagacacag ctagggctgt ttaccacaag gaaccagta ggcacacctc caccaaactg ggctctggt caagttcctt  2889 p94   ctccactttg acccagtcct tggtgcacag ccacctcaag tgtctggctt gctggagct ctgcagaogc tgtctacata gctgtaact gggttgtcca  2989 p94   cagcctgtc accatctgca ctcagttctg ccagtttag ggtgggtcta ctctggggtc ataggggtgt ggatacctga caaaatgtg gctacacttc  3089 p94   tgaaagaatc tatctaaata aaggcagca catggctggt tccaccatt  3138
```

Fig. 11

```
                                                                                                                              Domain I
R188 ---------- ---------- ---------- ---------- ---------- MPXIIPGFFC DRVIRERDRR NGEGIVSQPL KFEGQDFVVL KQRCLAQKCL FEDRVFPAGT QALGSHELSQ KAKMKAITWK     80
p94  MPTVISPIVA PRTGAEPRSP GPVPHPAQGK TTEAGGGHPG GIYSAIISRN FPIIGVKEKT FEQLHKKCLE KKVLYLDPEF PPDESLFYS QKPIQFVWK                                      100
                                           NS R188 RPKEICENPR FIIGGANRTD ICQGDLGDCW FLAAIACLTL NERLLFRVIP HDQSFTENYA GIFHFQFWRY GDWVDVVIDD CLPTANMQIV FTKSNHRNEF                                    180
p94  RPPEICENPR FIIGGANRTD ICQGDLGDCW LLAAIACLTL NERLLFRVIP HDQSFTENYA GIFHFQFWRY GDWVDVVIDD CLPTANMQIV FTKSNHRNEF                                    200

R188 WSALLEKAYA KLHGSYEALK GGNTEAMED FTGGVTEFFE IKDAPSIMYK IMRKAIERGS LMCCSIDDGT NMTYGTSPSG INMGELIARM VRNMDNSLLR                                    280
p94  WSALLEKAYA KLHGSYEALK GGNTEAMED FTGGVTEFFE IKDAPSIMYK IMRKAIERGS LMCCSIDDGT NMTYGTSPSG INMGELIARM VRNMDNSLLR                                    300
                                                                                        IS1

R188 DSDIDPRASD DRPSRTIVEV QYETRMACGL VKGHAYSVTG LEEALFKGEK VKLVFLRNPW GQVEWNGSWS DGWKDWSFVD KDEKARLQHQ VTEDGEFWMS                                   380
p94  DSDIDPRASD DRPSRTIVEV QYETRMACGL VKGHAYSVTG LEEALFKGEK VKLVFLRNPW GQVEWNGSWS DGWKDWSFVD KDEKARLQHQ VTEDGEFWMS                                   400
                                                                                                                                 Domain II
```

Fig. 12

| | | | | | | |
|---|---|---|---|---|---|---|
| Rt88 | YDDFVJHFTK | LEICNLTADA | LESDKLQIWT | VSVNEGRMVR | GCSAGGCRNF | PDTEWINFQY | RLKCLEEDDD | PDDSEVICSF | LVALMQKNRR | KDRKLGANLF | 480 |
| p94 | YDDFVJHFTK | LEICNLTADA | LESDKLQIWT | VSVNEGRMVR | GCSAGGCRNF | PDTEWINFQY | RLKCLEEDDD | PDDSEVICSF | LVALMQKNRR | KDRKLGANLF | 500 |

| Rt88 | TTIGFAIYEVP | KEMHGNKQHL | QKDFFLYNAS | KARSKTYINM | REVSQRFRLP | PSEYVTVPST | YEPHQEGEFI | LRVFSEKRNL | SEEAENTISV | DREV——— | 574 |
| p94 | TTIGFAIYEVP | KEMHGNKQHL | QKDFFLYNAS | KARSKTYINM | REVSQRFRLP | PSEYVTVPST | YEPHQEGEFI | LRVFSEKRNL | SEEAENTISV | DRVKKKQNK | 600 |

Domain III ▼          IS2

| Rt88 | ——————— | ——PR | PGHTDQESEE | QQQFRNIFRQ | IAGDMEICA | DELKNVLNIV | VNKHDLKTQ | GFTLESCRSM | 636 |
| p94 | PILFVSDRAN | SNKELGVDQE | AEGGKGKTGP | DKQGESFQPR | PGHTDQESEE | QQQFRNIFRQ | IAGDMEICA | DELKNVLNIV | VNKHDLKTQ | GFTLESCRSM | 700 |

| Rt88 | IALMDTDGSG | RLNLQEFHHL | WKKIKAWQKI | FKHYDTDHSG | TINSYEMRNA | VNDAGFHLNS | QLYDIITMRY | ADKHMNIDED | SFICCFVRLE | GMERAFHAFD | 736 |
| p94 | IALMDTDGSG | RLNLQEFHHL | WKKIKAWQKI | FKHYDTDHSG | TINSYEMRNA | VNDAGFHLNS | QLYDIITMRY | ADKHMNIDED | SFICCFVRLE | GMERAFHAFD | 800 |

| Rt88 | KDGDGIIKLN | VLEWLQLTMY | A | 757 |
| p94 | KDGDGIIKLN | VLEWLQLTMY | A | 821 |

Domain IV ▼

Fig. 14
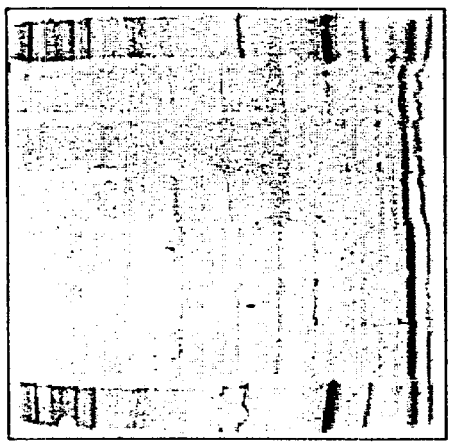
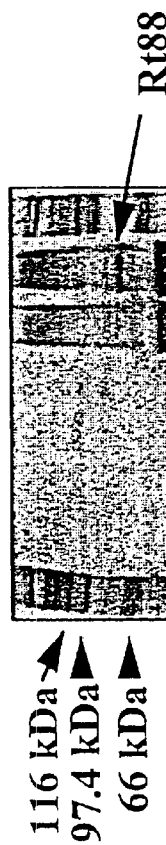
Std. molecular weigh marker
1. before introduction of expression
2. 1 hour after introduction of expression  } soluble protein
3. 4 hours after introduction of expression
4. before introduction of expression
5. 1 hour after introduction of expression  } insoluble protein
6. 4 hours after introduction of expression 1: 1kbp DNA ladder
2: Rt88 gene transferred 293 cells-1
3: Rt88 gene transferred 293 cells-2
4: only vector transferred 293 cells
5: 6-week old rat retina

CALPAIN AND DNA ENCODING THE SAME

This is a 371 application of PCT/JP99/00903 filed Feb. 26, 1999.

FIELD OF THE INVENTION

The present invention relates to newly identified calpain, Rt88 protein, which has been of the retina in eye tissues, and a DNA encoding it.

BACKGROUND OF THE INVENTION

Calpain is present, in particular, in the cytoplasm of animal cells and is a cysteine protease which is activated by calcium. Several molecular species have been known in calpain. For analyzing the structure, their cDNA's have been cloned and, at present, the presence of μ-and m-calpain which are generally expressed in various tissues, as well as tissue-specific calpain such as, for example, p94 which is specifically expressed in a skeleton muscle is revealed [Seikagaku (Biochemistry), Vol. 65, No. 7, pp. 537–552 (1993); Jikken Igaku (Experimental Medicine), Vol. 13, No. 9, pp. 35–42 (1995)].

Although details of physiological functions of calpain are not yet elucidated, calpain has been considered to have functions of a calcium receptor in cells and to be concerned in, for example, signal transduction, control of transcription, propagation and differentiation of cells, and the like.

Recently, it has been reported that a mutant gene of calpain p94 specifically expressed in a skeleton muscle is one of causative genes of a kind of dystrophy, myodystropy, which is known to be a disease wherein differentiated cells fall into spontaneous degeneration or atrophy without any anticipation disorder such as inflammation or injury (Isabelle Richard et al., Cell, 81, 28–40 (1995)). In addition, it has been found that p94 protein is decreased in myodystrophy (Melissa J. Spencer et al., Journal of the Neurological Science, 146, 173–178 (1997)).

On the other hand, in general, retinal degenerative diseases are divided into dystrophy and other degenerative diseases. Dystrophy is hereditary and, in many cases, the prognosis of vision is pessimistic. Then, dystrophy is of importance from clinical viewpoint (Yoshihiro Hotta, "The Cause of Retinal Degeneration" in Atarashii Ganka (Journal of the Eye), 13 (7): 993–1001, 1996). In particular, at present, pigmentary retinal degeneration is designated as an objective disease in the Ministry of Health and Welfare Research Work for Treatment of Specific Diseases.

However, no study of the relation between dystrophy and calpain in retinal degenerative diseases has been found heretofore in the prior art.

OBJECTS OF THE INVENTION

The main object of the present invention is to investigate calpain which is tissue-specifically expressed in the retina of eye tissues, to isolate its gene, to determine the structure of a protein and to use them in studies of diseases in ophthalmologic field and in treatment and prevention of diseases in ophthalmologic field, in particular, retinal degenerative diseases.

This object as well as other objects and advantages of the present invention will become apparent to those skilled in the art with reference to the attached drawings.

BRIEF EXPLANATION OF DRAWINGS

FIGS. 3A and 3B are photographs showing electrophoretic migration patterns of the PCR products No. 3 and No. 4 in FIG. 1, respectively.

FIG. 5 illustrates a comparison of the cDNA sequence obtained in Example 1 hereinafter with that of p94.

FIG. 6 illustrates a comparison of the cDNA sequence obtained in Example 1 hereinafter with that of p94 (continued FIG. 5).

FIG. 7 illustrates a comparison of the cDNA sequence obtained in Example 1 hereinafter with that of p94 (continued FIG. 6).

FIG. 8 illustrates a comparison of the cDNA sequence obtained in Example 1 hereinafter with that of p94 (continued FIG. 7).

FIG. 10 illustrates a comparison of the cDNA sequence obtained in Example 1 hereinafter with that of p94 (continued FIG. 9).

FIG. 11 illustrates a comparison of an amino acid sequence deduced from the cDNA of SEQ ID NO: 2 with the amino acid sequence of p94.

FIG. 12 illustrates a comparison of an amino acid sequence deduced from the CDNA of SEQ ID NO: 2 with the amino acid sequence of p94 (continued FIG. 11).

FIG. 14 illustrates electrophoretic migration patterns of a protein reacted with the Rt88 antibody obtained in Example 5 hereinafter.

SUMMARY OF THE INVENTION

Figure 1:
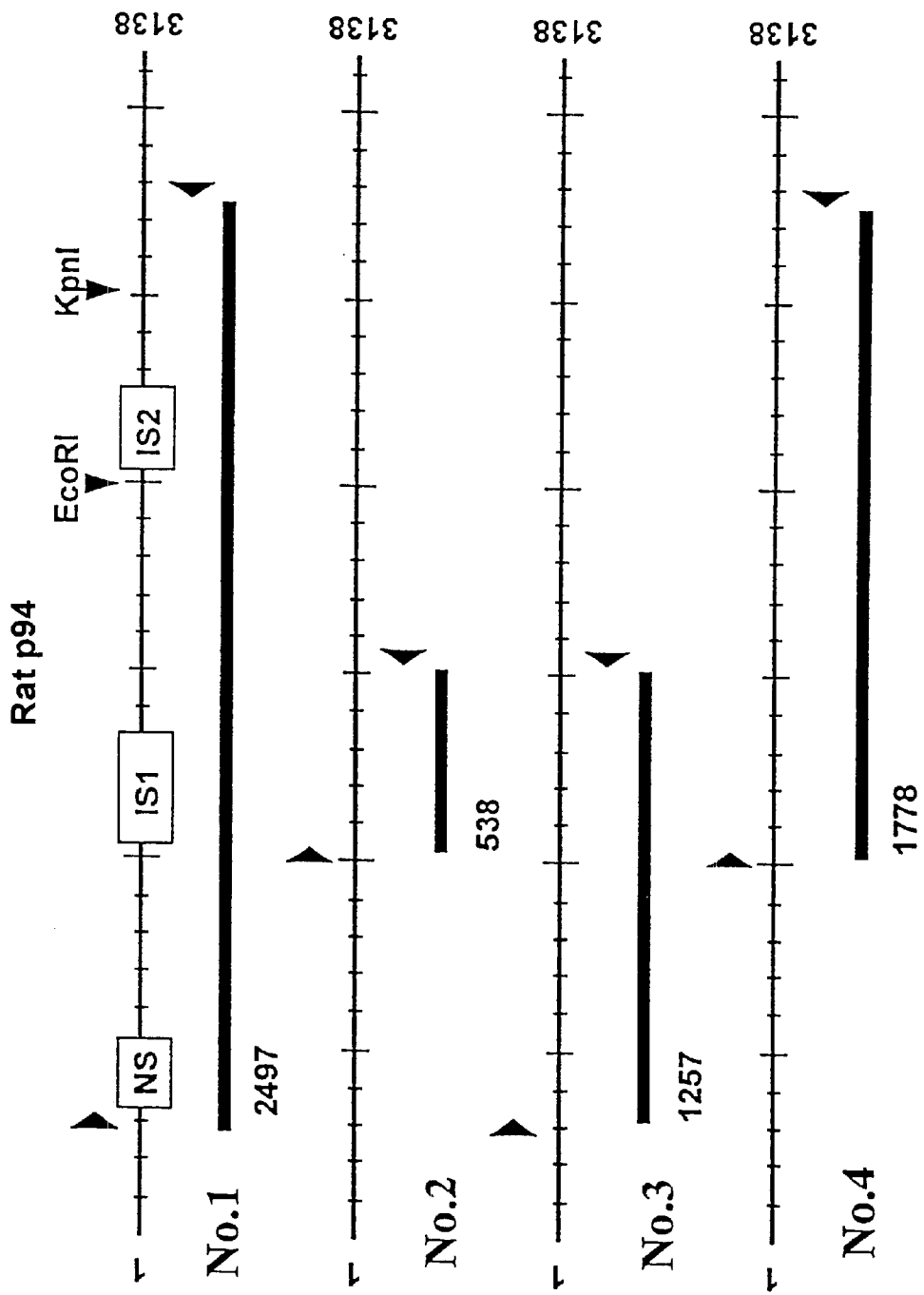
FIG. 1 illustrates a combination of four primers and size of the products amplified by RT-PCR in Example 1 hereinafter.

Since calpain is concerned with myodystrophy, the present inventors have expected that, it calpain which is tissue-specifically expressed in eye tissues can be found out, new routes for studying dystrophy in retinal degenerative diseases can be provided, and causes of, for example, retinopathy can be elucidated by examining an expression amount and gene mutation of this calpain in retinopathy, and that further improvement of the examination can establish therapy of such a disease. In view of the above, the present inventors have studied intensively.

That is, for the purpose of finding out novel calpain, the present inventors have designed primers based on a DNA of skeleton muscle-specific calpain, p94, and have succeeded in obtaining a DNA (CDNA) encoding new calpain from a total RNA of a rat retinal tissue by using RT-PCR technique and 5' RACE. Based on the sequence of this cDNA, an amino acid sequence of this calpain has been deduced.

Expression of the cDNA by a host can be expected to produce a protein corresponding to the calpain. In addition, the calpain can be expected to be used as an reagent in studies in connection with, for example, differentiation, growth, propagation, life conservation, and signal transduction of animal cells. Further, it can be expected to be used as medicine for elucidating and treating diseases.

The present invention has been completed based on these findings and provides a protein having an amino acid sequence represented by SEQ ID NO: 1 in the Sequence Listing, in particular, a protein corresponding to calpain derived from the retina.

The present invention also provides a DNA encoding the protein, a vector comprising the DNA and a transformant transformed with the vector. The DNA includes a nucleotide sequence represented by SEQ ID NO: 2 in the Sequence Listing and those hybridizable with it under stringent conditions.

Further, the present invention provides a process for producing the protein which comprises culturing the transformant in a culture medium to produce and accumulate the protein having the amino acid sequence represented by SEQ ID NO: 1 in the culture.

Furthermore, the present invention provides a inhibitor to the protein of the present invention; a pharmaceutical composition for treating or preventing retinal disorders which comprises an anti-sense DNA, anti-sense RNA or sense DNA of a MRNA for translating the protein or a triplet DNA of a genomic DNA expressing a mRNA for translating the protein; and a composition for retina diagnosis which comprises a genomic DNA expressing a mRNA for translating the protein.

DETAILED DESCRIPTION OF THE INVENTION

The protein of the present invention includes a protein having a molecular weight of about 88 kDa and having an amino acid sequence represented by SEQ ID NO: 1 of the Sequence Listing, and a protein containing the protein in its molecule. In particular, the protein having the protease activity of calpain. Although there are many isozymes in calpain, they have the same basic skeleton which is divided into four functional domains (see FIG. 11 and FIG. 12). The protease activity of calpain is derived from Domain II which is a protease region having homology to a cysteine protease.

The protease activity of calpain can be represented by its capability of decomposing a substrate protein. Examples of the substrate include cytoskeletal protein (e.g., spectrin, MAP-2, tau factor, neurofilaments H, M and L, α-actinin), membrane-binding receptor protein (e.g., EGF receptor, AMPA receptor, calcium pump, anion channel, calcium release channel, L-type calcium channel, G-protein), calmodulin-binding protein (e.g., calcium pump, calcineurin, CaM-dependent protein kinase II, myosin L-chain kinase, neuromodulin, connexin, IP3 kinase), enzyme (e.g., protein kinase C, HMG-CoA reductase, cAMP-dependent kinase, pyruvate kinase, phosphorylase kinase), myofibril protein (e.g., troponin I, troponin T, tropomyosin, myosin), transcription factor (e.g., c-fos, c-jun, Pit-1, Oct-1, CP1a and b, c-Myc) and the like (Kevin K. Wand and Po-wai Yuen, Adv. Pharmacol., 37, 117–152 (1997)). The capability of decomposing a substrate protein can be determined by a known method. For example, by using FITC casein as a substrate, the intensity of fluorescence of a FITC casein fragment in an acid soluble fraction decomposed from the substrate can be determined (David, L. L. and Shearer, T. R., Exp. Eye Res., 42, 227–238 (1986)). One unit of calpain used herein is defined as an amount of an enzyme which releases one pg of a FITC casein fragment per one minute.

The calpain of the present invention is considered to be one of calpain families specifically expressed only in the retina in view of the expression state of its mRNA in each tissue.

The DNA of the present invention can be obtained by, first, extracting a total RNA from a rat tissue with a commercially available kit for extracting a total RNA according to a protocol attached thereto.

Then, regarding the total RNA obtained, 3' terminus-cloning is carried out by RT-PCR with gene specific primers (GSP's) designed based on a cDNA sequence of known skeletal muscle-specific calpain, p94. For example, the total RNA is subjected to a reverse transcription reaction with oligo dT primer and the resultant cDNA is amplified with sense and anti-sense GSP's having the sequence represented by SEQ ID NOS: 3 to 6. This PCR product is sub-cloned with, for example, a commercially available cloning kit to conduct 3' terminus-cloning, thereby determining the 3' terminus nucleotide sequence.

On the other hand, since the 5' terminus of a retina-derived CDNA cannot be amplified by PCR, a nucleotide sequence is determined by 5' RACE. For example, the above-extracted total RNA is subjected to a reverse transcription reaction similar to that in the sequence determination of the 3' terminus by using a commercially available 5' RACE system to prepare a cDNA for a first strand. However, as the anti-sense primer, the GSP having the sequence of SEQ ID NO: 6 is used. After purification of the cDNA thus prepared, TdT is added thereto and the resultant cDNA is amplified by PCR. As the sense primer, that of the protocol of the kit is used, and the GSP having the sequence of SEQ ID NO: 7 is used as the anti-sense primer. According to the same manner as that described above, the PCR product is subjected to sub-cloning to determine the 5' terminus nucleotide sequence.

The fact that the 5' terminus of a retina-derived cDNA cannot be amplified by primers based on the cDNA sequence of the skeleton muscle-specific calpain, p94 shows that the sequence of the 5' terminus is different from that of p94.

The whole nucleotide sequence is determined based on respective nucleotide sequences of 3' and 5' termini thus determined. Thus, the nucleotide sequence represented by SEQ ID NO: 2 has been determined. Differences between the sequence represented by SEQ ID NO: 2 and the skeleton muscle-specific calpain, p94, are recognized at exon 1 and exons 15 and 16.

SEQ ID NO: 1 represents a novel amino acid sequence deduced from the open reading frame of the nucleotide sequence of cDNA thus determined. The nucleotide sequence from 67th base to 2337th base encodes the protein of SEQ ID NO: 1.

The DNA of the present invention includes that hybridizable with the above sequence under stringent conditions. The stringent conditions mean that sequences hybridize to each other only when they have 95% or more homology. For example, the stringent conditions include such conditions as incubation in a solution containing 50% formaldehyde, 5×SSC (150 mM NaCl, 15 mM trisodium citrate), 50 mM sodium phosphate (pH 7.6), 5×Denhartdt's solution, 10% dextran sulfate and 20 μg/ml denatured salmon sperm DNA at 42° C. overnight, and then washing with 0.1×SSC at about 65° C.

The DNA of the present invention can integrate into a vector according to a conventional method, for example, by ligation with T4DNA ligase which is an enzyme to join 5'—P end and 3'—OH end of DNAs to ligate a DNA to be inserted to the vector. As a vector for expressing a protein, for example, pQE (QIAGEN), pET (NOVAGEN), pTrcHis (Invitorogen) and the like can be used.

Further, the present invention provides a transformant prepared by transforming host cells with an expression vector into which the DNA of the present invention has been integrated. Transformation can be carried out according to a conventional method such as that using competent cells obtained by treatment with calcium chloride, electroporation, and the like. For example, E. coli cells, cultured cells and the like which are capable of incorporating a foreign DNA can be used as the competent cells. As the host cells, both eukaryotic cells and prokaryotic cells can be used. For example, animal cells (COS cell, fibroblast or epithelial cell, lymphocyte, hematopoietic cell, ES cell, etc.), baculovirus, yeast, E. coli, Xenopus laevis oocyte, wheat germ, reticulocyte and the like can be used.

The protein of the present invention can be obtained by culturing the transformant thus obtained according to a conventional method. The protein of the present invention is produced in the cytoplasm.

For separation and purification of the protein of the present invention, for example, microbial cells or cells are collected after culturing them by a known method, and they are disrupted in a suitable buffer solution by sonication or the like, followed by centrifugation or the like to obtain the protein as a crude extract. The buffer solution may contain a protein denaturant such as urea, guanidine hydrochloride, etc., and a surfactant such as Triton, etc. When the protein or the like is secreted in a culture medium, microbial cells or cells are separated after culturing them according to a per se known method to collect the supernatant. Purification of the protein of the present invention thus obtained can be carried out by appropriately combining known methods, for example, salting out, gel filtration, SDS-polyacrylamide gel electrophoresis, affinity chromatography and the like. When the protein is obtained in its free form, it can be converted into a suitable salt by a per se known method [for example, salts with alkali metals (e.g., sodium, potassium, etc.), addition salts with inorganic acids (e.g., hydrochloric acid, phosphoric acid, hydrobromic acid, sulfuric acid, etc.), addition salts with organic acids (e.g., acetic acid, formic acid, propionic acid, fumaric acid, maleic acid, succinic acid, tartaric acid, citric acid, benzoic acid, methanesulfonic acid, benzenesulfonic acid, etc.)]. On the other hand, when the protein is obtained as a salt, it can be converted into its free form by a per se known method.

In the protein of the present invention, its C-terminus may be in the form of an amide ($—CONH_2$) or an ester (—COOR), wherein R of the ester is, for example, a lower alkyl group such as methyl, ethyl, propyl, butyl, etc., an aryl group such as phenyl, naphthyl, etc., an aralkyl group such as benzyl, phenethyl, etc., pivaloyloxymethyl group or the like. In addition, the protein of the present invention includes that wherein its carboxyl (—COOH) or carboxylate ($—COO^-$) group other than such a group at the C-terminus is amidated or esterified as above. Further, the protein of the present invention includes a protected protein wherein a substituent on a side chain of the amino acid in the molecule (e.g., hydroxyl group, thiol group, amino group, guanidino group, etc.) is protected with a suitable protecting group (e.g., formyl group, an acyl group, etc.), or a protein to which a saccharide chain is attached.

The presence or activity of the protein or its salt of the present invention thus obtained can be confirmed by immunoblotting technique using a specific antibody, the protease activity of the above calpain, and the like.

An antibody against the protein or its salt of the present invention may be any polyclonal or monoclonal antibody as far as it can recognize the protein of the present invention. The antibody against the protein of the present invention can be produced according to a per se known process for producing an antibody or antiserum. For example, an immunogen itself such as the protein of the present invention, the peptide of SEQ ID NO: 11 or the like, or a complex thereof with a carrier protein is prepared and a mammal is immunized with it. A material containing an antibody against the protein of the present invention or the like is collected from the immunized animal and the antibody is separated and purified. Examples of the mammal include rabbit, guniea pig, mouse, rat and the like. When the antigen is administered, a complete adjuvant or an incomplete adjuvant may also be administered to enhance the antibody productivity. Normally, it is administered once every 2 to 6 weeks, about 2 to 10 times in all. The antibody can be collected from blood of the immunized animal. An antibody titer can be measured by dot blotting technique, ELISA, etc. Separation and purification of the antibody can be carried out according to that of an immunoglobulin.

The protein obtained is retina specific calpain and there is a high possibility that this is concerned in various retinal diseases, because a possible pathogenesis of retinal diseases is considered to be a mutant gene of calpain, and manifestation of various diseases is considered to be excess expression of a gene of this retina specific calpain and its protein or failure of expression thereof due to physical disorders.

Therefore, the protein of the present invention can be used as an agent useful for diagnosis, or prevention and treatment of various retinal diseases. In addition, it can be used for screening such an agent, and the like. Further, it can be used for researches of these diseases, and the like.

For example, it is considered that retinal diseases are manifested by an abnormal rise in the protein of the present invention due to ischemia, retinal neovascularization, or the like. Then, an inhibitor of the protein which can be selected by measuring a protease activity using FITC casein as a substrate is useful as an agent for preventing and treating these diseases.

In addition, it is also considered that retinal diseases are manifested by a rise in expression of a mRNA for translation of the protein of the present invention due to ischemia, retinal neovascularization, or the like. Then, these diseases can be treated by injecting retroviruses or cationic liposomes, into which an antisense DNA, a triplet DNA or an antisense RNA has been integrated, in the vitreous or subretinal cavity. Further, they can be treated by transplanting gene transferred cells. The antisense DNA can be obtained as a DNA hybridizable to a mRNA of the protein of the present invention. The triplet DNA can be obtained as a DNA hybridizable to a genomic DNA which expresses a mRNA of the protein of the present invention. The antisense RNA can be obtained as a RNA hybridizable to a mRNA of the protein of the present invention.

Further, since there is a report about hereditary pigmentary retinal degeneration due to pint mutation of rhodopsin gene [K. Kajiwara, Atarashii Ganka (Journal of the Eye), 12(2): 239–250, 1995], it is considered that a mutant gene of retina derived calpain also causes retinal diseases. These diseases can be treated by injecting a vector, into which a sense DNA to a mRNA for translation of the protein of the present invention has been integrated, in the vitreous or subretinal cavity, or by transplanting gene transferred cells to express the protein.

Furthermore, retinal diseases can be diagnosed by collecting a genomic DNA from a retina or blood sample of a patient to confirm a mutant gene by SSCP (single-stranded conformation polymorphism), DGGE (denaturing gradient gel electrophoresis), differential display, or the like.

The following Examples further illustrate the present invention in detail but are not to be construed to limit the scope of the present invention.

EXAMPLE 1

(1) Extraction of Total RNA From Each Tissue

Each tissue (lens, retina, brain, and muscle), of a 14-day old Sprague-Dawley male rat was removed and the total RNA was extracted therefrom according to the protocol of a total RNA extraction kit, TRIzol™ agent (Life Technologies).

First, TRIzol™ agent was added to the tissue (1 ml/100 mg tissue). The mixture was homogenized and the homogenate was incubated at room temperature for 5 minutes. Chloroform (0.2 ml/ml TRIzol™ agent) was added thereto and the mixture was shaken lightly for 15 seconds. After shaking, the mixture was incubated at room temperature for 5 minutes and centrifuged at 12,000×g at 4° C. for 15 minutes. After centrifugation, the supernatant was transferred to a new tube and isopropanol (0.5 ml) was added thereto. The mixture was shaken lightly and further centrifuged at 12,000×g at 4° C. for 15 minutes. When a pellet was confirmed, it was washed once or twice with 75% ethanol. Then, the pellet was dissolved in RNase and DNase-free water and the concentration was measured by the absorbance A260/280.

(2) 3' Terminus-cloning

GSP's for PCR were designed based on the cDNA sequence (3138 bases) of skeleton muscle-specific calpain p94, and four (4) PCR products were obtained by changing combination of GSP's.

SEQ ID NOS: 3, 4, 5 and 6 of the Sequence Listing represent the sense and antisense sequences used. specifically, a reverse transcription reaction about the total retinal RNA extracted in the above (1) was carried out at 42° C. for 50 minutes and then 70° C. for 15 minutes by using oligo dT primer. Then, the resultant cDNA was amplified by repeating a PCR cycle of 94° C. for 1 minute, 53° C. for 1 minute and then 72° C. for 3 minutes, 30 times using the combination of GSP's of SEQ ID NOS: 3 and 4 in the Sequence Listing; a PCR cycle of 94° C. for 45 seconds, 53° C. for 45 seconds and then 72° C. for 1 minutes, 35 times using the combination of GSP's of SEQ ID NOS: 5 and 6 in the Sequence Listing; a PCR cycle of 94° C. for 1 minute, 53° C. for 1 minute and then 72° C. for 2 minutes, 30 times using the combination of GSP's of SEQ ID NOS: 3 and 6 of the Sequence Listing; And a PCR cycle of 94° C. for 1 minute, 53° C. for 1 minute and then 72° C. for 2 minutes, 30 times using the combination of GSP's of SEQ ID NOS: 4 and 5 of the Sequence Listing to obtain PCR products of 2497 bases, 538 bases, 1257 bases and 1778 bases, respectively (FIG. 1, No. 1–No. 4).

In FIG. 1, NS represents a novel sequence and IS 1 and 2 represent insertion nucleotide sequences 1 and 2.

After amplification of the cDNA's with the primer combinations as those described with respect to FIG. 1, No. 1–No. 4, the resultant PCR products were subjected to electrophoresis using 1.0% agarose gel for the primer combination in No. 1, 1.5% agarose gel for the primer combination in No. 2 and 1.2% agarose gel for both primer combinations in Nos. 3 and 4, respectively, in TAE buffer (Life Technologies) at 75 V for about 1 hour.

Figure 2:
FIGS. 2A and 2B are photographs showing electrophoretic migration patterns of the PCR products No. 1 and No. 2 in FIG. 1, respectively.

The electrophoretic migration patterns are shown in FIGS. 2 and 3. FIG. 2A is the patterns of the PCR products using the primer combination of No. 1. In FIG. 2A) the lanes 1 and 6 are 1 kbp DNA ladder; the lane 2 is the product derived from the lens tissue; the lane 3 is the product derived from the retinal tissue; the lane 4 is the product derived from the brain tissue; and the lane 5 is the product derived from the muscle. FIG. 2B is the patterns of the PCR products using the primer combination of No. 2. In FIG. 2B, the lanes 1 and 6 are 100 b DNA ladder; the lane 2 is the product derived from the lens tissue; the lane 3 is the product derived from the retinal tissue; the lane 4 is the product derived from the brain tissue; and the lane 5 is the product derived from the muscle. FIG. 3A is the patterns of the PCR products by the primer combination in No. 3. In FIG. 3A, the lane 1 is the product derived from the lens tissue; the lane 2 is the product derived from the retinal tissue; the lane 3 is the product derived from the brain tissue; the lane 4 is the product derived from the muscle; and the lane 5 is 1 kbp ladder. FIG. 3B is the patterns of the PCR products by the primer combination in No. 4 and respective lanes are the same as those in FIG. 3A.

As seen from these figures, in the retina, the 3' side was amplified, while the 5' side was not amplified. Therefore, it has been shown that the 5' side sequence is different from that of p94.

Figure 4:
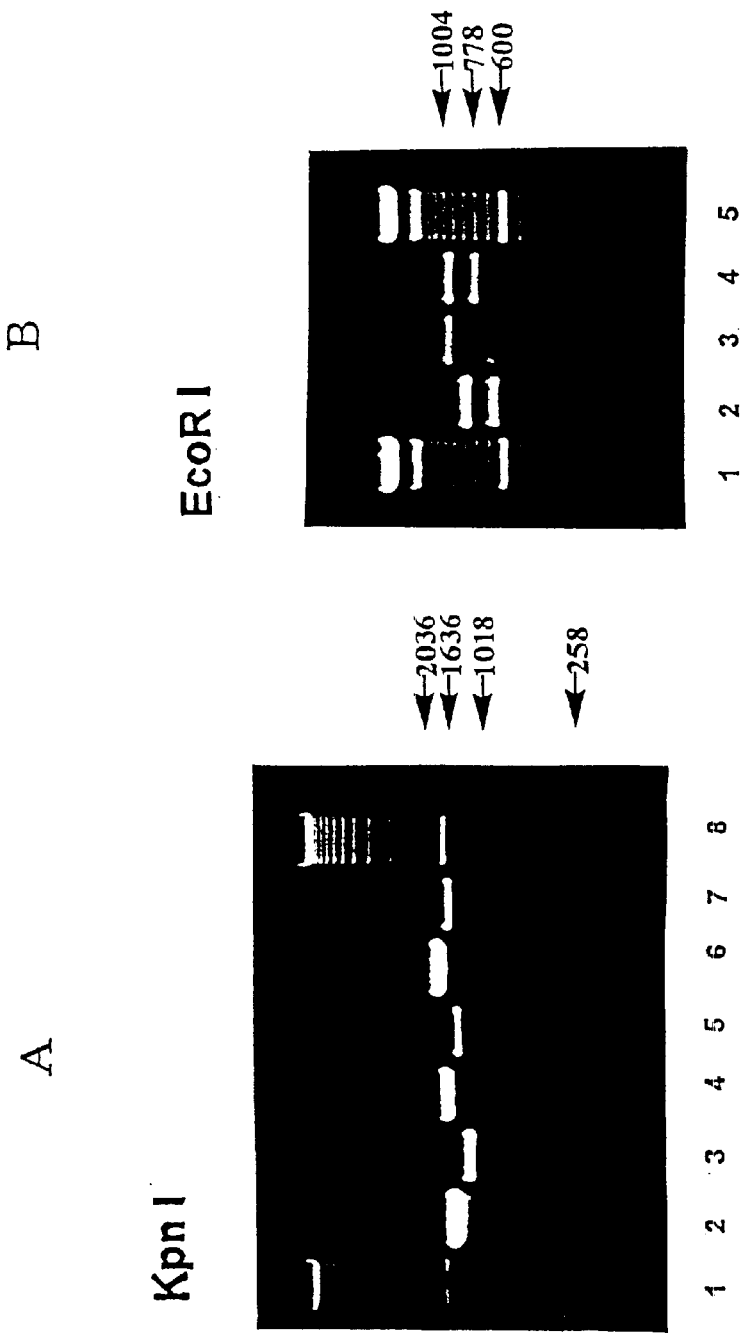
FIGS. 4A and 4B are photographs showing an electrophoretic migration pattern of the PCR product No. 4 in FIG. 1 after digestion with restriction enzymes KpnI and EcoRI.
Figure 9:
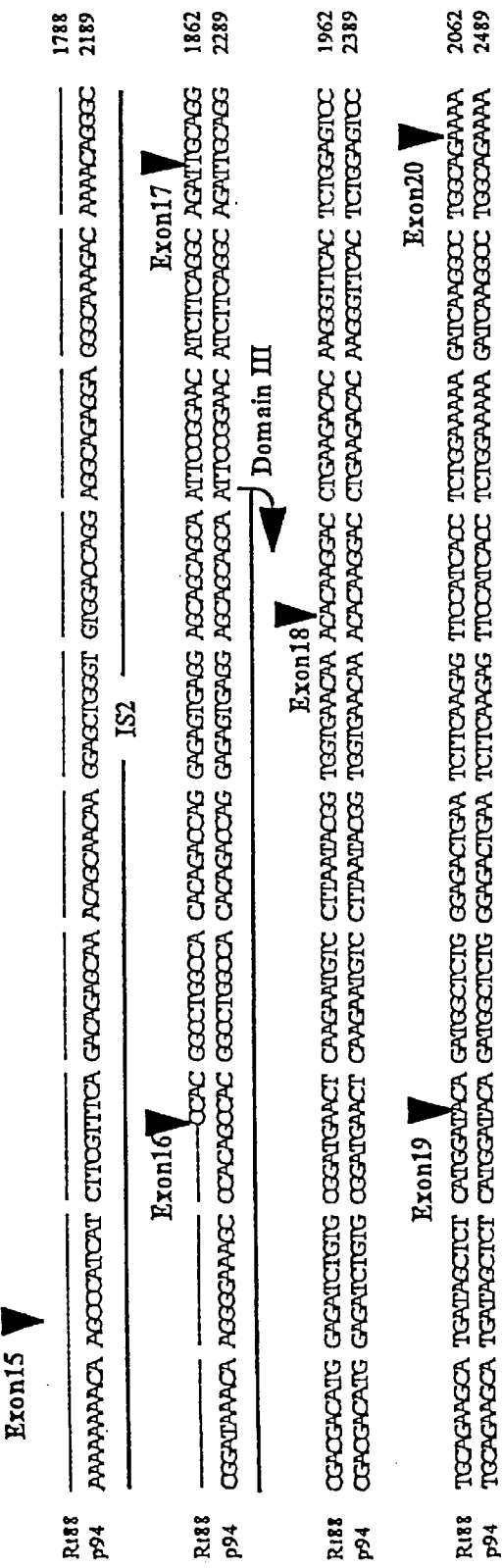
FIG. 9 illustrates a comparison of the cDNA sequence obtained in Example 1 hereinafter with that of p94 (continued FIG. 8).

FIG. 4 is similar electrophoretic migration patterns of cDNA's amplified with the primer combination in No. 4 of FIG. 1 and digested with the restriction enzymes KpnI (FIG. 4A) and EcoRI (FIG. 4B). The restriction sites are shown in FIG. 1. In FIG. 4A, the lanes 1 and 8 are 1 kbp DNA ladder; the lanes 2 and 3 are the KpnI-digested product derived from the lens; the lanes 4 and 5 are the KpnI-digested product derived from the retina; and the lane 6 and 7 are the KpnI-digested product derived from the muscle. In FIG. 4B, the lanes 1 and 5 are 100 bp DNA ladder; the lane 2 is the EcoRI-digested product derived from the lens; the lane 3 is the EcoRI-digested product derived from the retina; and the lane 4 is the EcoRI-digested product from the muscle. As seen from these figures, the size of the PCR products derived from the lens, retina and muscle tissues are different from one another.

A cDNA amplified with the GSP combination of No. 4 in FIG. 1 was sub-cloned according to a method of TA Cloning™ Kit (Invitrogen).

That is, the PCR product (1 µl) was subjected to ligation together with T4 ligase at 14° C. overnight, followed by transformation into competent cells. The transformed *E. coli* was plated on a LB plate and incubated at 37° C. overnight. A colony grown on the plate was incubated in a Terrific broth [containing select peptone 140 (11.8 g), yeast extract (23.6 g), dipotassium hydrogen phosphate (9.4 g), and potassium dihydrogen phosphate (2.2 g) per 1 liter, added thereto glycerol (4 ml/l); Life Technologies] at 37° C. overnight.

A plasmid DNA was prepared from the *E. coli* cultured overnight by using QIAprep Spin Miniprep Kit (QUIAGEN). That is, the broth containing the *E. coli* was centrifuged at 12,000×g to recover the *E. coli*, and to this was added buffer solutions P1 and P2 (250 µl), followed by shaking lightly. After standing for 5 minutes, buffer solution N3 (350 μl) was added thereto and the mixture was centrifuged at 12,000×g for 15 minutes. After centrifugation, the supernatant was transferred to a column and centrifuged at 12,000×g for 30 seconds. Further, PB (0.5 ml) was added thereto to wash the column, followed by addition of buffer solution PE (0.75 ml) and centrifugation at 12,000×g for 30 seconds. The plasmid DNA adhered to the column was dissolved in DNase-free water (45 μl) to recover the DNA. The plasmid DNA was digested with the restriction enzyme EcoRI and a positive clone was selected to determine its nucleotide sequence.

(3) 5' Terminus-cloning

The 5' terminus sequence was determined by 5' RACE. The total retinal RNA (4 μg) extracted in the above (1) was subjected to 5' RACE according to the protocol of 5' RACE system version 2.0 (Life Technologies). First, the total retinal RNA (4 μg) was subjected to a reverse transcription reaction at 42° C. for 50 minutes and 70° C. for 15 minutes to prepare a 1st strand cDNA. In this reaction, the GSP having the sequence represented by SEQ ID NO: 6 of the Sequence Listing was used as the antisense primer. The 1st strand cDNA thus prepared was purified by GLASS MAX and TdT was added thereto. The resultant cDNA was amplified by PCR. As the sense primer, that of the protocol of the kit was used and the GSP having the sequence represented by SEQ ID NO: 7 of the Sequence Listing was used as the antisense primer. PCR was carried out by repeating a PCR cycle of 94° C. for 1 minute, 55° C. for 1 minute and then 72° C. for 2 minutes, 35 times.

The PCR product was subjected to sub-cloning according the same manner as described in the above (2).

The whole nucleotide sequence was determined based on the above-obtained respective nucleotide sequences at 3' terminus and 5' terminus. The whole nucleotide sequence of the cDNA determined is shown in SEQ ID NO: 2 of the Sequence Listing. Further, FIGS. 5 to 10 show comparison of the CDNA sequence (Rt88) and the cDNA sequence (p94) of rat skeleton muscle-specific calpain p94.

In comparison with rat skeleton muscle-specific calpain p94, the DNA sequence of the novel calpain of the present invention differs from p94 in exon 1 and exons 15 and 16. That is, differences were observed in NS region and a part of IS 2 region of p94. In addition, when expression of a mRNA corresponding to this sequence in each eye tissue, brain and muscle tissue in rat was observed, it was expressed specifically in the retina. In view of this, it is considered that the cDNA obtained by the present invention is one of families of calpain specifically expressed in the retina.

Further, an amino acid sequence was deduced from the cDNA sequence thus determined to obtain the amino acid sequence represented by SEQ ID NO: 1 of the Sequence Listing. FIGS. 11 and 12 show comparison of the amino acid sequence (Rt88) with that of p94 represented by the single letter abbreviation.

EXAMPLE 2

Construction of Transfer Vector

GSP's for PCR containing initiation and termination codons respectively were designed based on the cDNA sequence of the novel calpain obtained in the above (2) and (3) in Example 1.

The total retinal RNA extracted in Example 1 (1) was subjected to a reverse transcription reaction using oligo dT primer at 42° C. for 50 minutes and then 70° C. for 15 minutes. Then, the resultant cDNA was amplified by repeating a PCR cycle of 94° C. for 1 minute, 53° C. for 1 minute and 72° C. for 3 minutes, 35 times by using the GSP's represented by SEQ ID NOS: 8 and 4 in the Sequence Listing as the sense and antisense primers, respectively. The PCR product was sub-cloned according to a method of TA Cloning Kit (Invitrogen).

That is, the PCR product (1 μl) was inserted into pCR2.1 by ligation together with T4 ligase at 14° C. overnight. *E. coli* K12 was transformed with this to obtain a transformant. The transformant was named *Escherichia coli* K12/Rt88 and have been deposited at National Institute of Bioscience and Human Technology (NIBH), Agency of Industrial Science & Technology, Ministry of International Trade & Industry of 1–3, Higashi 1 chome, Tsukuba-shi, Ibaraki-ken, Japan under the accession number of FERM BP-6237 according to the Budapest treat since Jan. 26, 1998.

EXAMPLE 3

Northern Blotting Technique

Test Method

Northern blotting analysis is composed of (1) extraction of a total RNA from a tissue, (2) electrophoresis of the total RNA and transcription to a membrane, (3) preparation of a probe, (4) hybridization of the probe and the transcribed RNA, and (5) detection of the hybridized RNA.

(1) Extraction of Total RNA From Tissue

According to the same manner as described in Example 1 (1), a total RNA was extracted from each tissue of a 6-week old Sprague-Dawley male rat. Specifically, a total RNA of each tissue was collected and homogenized in TRIzol reagent. Then, chloroform (0.2 ml/ml TRIzol reagent) was added thereto to prepare a suspension and the suspension was allowed to stand at room temperature for 5 minutes. After standing, it was centrifuged at 12,000×g at 4° C. for 15 minutes to separate into a total RNA layer, a protein layer and a DNA layer. Then, The upper layer containing the total RNA was recovered and propyl alcohol (0.5 ml/ml TRIzol reagent) was added thereto to prepare a suspension. After allowing to stand at room temperature for 10 minutes, the suspension was centrifuged at 12,000×g at 4° C. for 10 minutes to precipitate the total RNA. The precipitated total RNA was washed with 75% ethanol and air-dried for 10 minutes to remove ethanol. Finally, it was dissolved in RNase-free water and the concentration was measured at an absorbance A260/280.

(2) Electrophoresis of Total RNA and Transcription to Membrane

Electrophoresis and transcription of the total RNA were carried out according to NorthernMax™ (Ambion). Specifically, first, DEPC treated water (90 ml) was boiled and agarose (1 g) was dissolved therein. After cooling to 50 to 60° C., 10×denaturing gel buffer (10 ml) was added and the mixture was stirred and poured into an electrophoresis apparatus. After solidification, the gel was soaked in 1×MOPS gel running buffer. To the total RNA extracted and purified by the method of the above (1) were added 3-fold amount of formaldehyde load dye and then ethidium bromide solution (1 μl, concentration: 200 g/ml, Life Technologies). Then, the resultant solution was heated at 65° C. for 15 minutes to break the secondary structure of total RNA and then subjected to electrophoresis at a constant voltage of 50 V. After electrophoresis, bands of the total RNA were confirmed by a UV transilluminater and a photograph of the migration pattern was taken by a Polaroid camera. Blotting was carried out in 0.5×TBE buffer (Life Technologies) with a blotting device of TEFCO at a constant voltage of 25 V for 2 hours. After blotting, the membrane was air-dried for 30 minutes and then UV (50 mj) was irradiated with GS GENE linker UV CHANBER (Bio-Rad) to bind the total RNA to the membrane.

(3) Preparation of Probe

For detecting Rt88 mRNA, a probe was prepared. Specifically, first, a partial sequence of Rt88 cDNA was amplified by PCR for detecting Rt88 mRNA. PCR was carried out by adding the template DNA, the full-length Rt88 cDNA (1 ng), primers (0.2 μM, sense primer: SEQ ID NO: 9, and antisense primer: SEQ ID NO: 10) and Taq DNA polymerase (2.5 U, Life Technologies) to 1×PCR buffer [20 mM Tris-HCl (pH 8.4), and 50 mM KCl ], 2 mM $MgCl_2$ and 0.2 mM dNTP. The PCR cycle of 94° C. for 45 seconds, 58° C. for 45 seconds and then 72° C. for 1 minute was repeated 35 times. The amplified fragment was subjected to ligation to integrate it into a vector containing T7 promoter (pCR2.1) according to the protocol of TA Cloning Kit (Invitrogen). The reaction was carried out at 14° C. for 4 hour or more by using 1×ligation buffer, pCR2.1 (50 ng), the PCR product (10 ng or more) and T4 DNA ligase (4.0 Weiss units). Then, it was transformed into E. coli. Specifically, first, 0.5 M β-mercaptoethanol (2 μl ) was added to one shot competent cells (50 μl ) and, further, a solution after the ligation (1 μl ) was added thereto. The mixture was allowed to stand in ice for 30 minutes. Then, heat treatment was carried out at 42° C. for 30 seconds. Immediately after the heat treatment, the mixture was put back in ice and allowed to stand for 2 minutes. Then, SOC medium (230 μl) was added and the mixture was incubated at 37° C. for 1 hour. Finally, the incubated cells were plated on LB medium (Life Technologies) containing ampicillin (100 μg/ml, Life Technologies), 100 μM IPTG (Life Technologies) and X-gal (40 μg/ml, Life Technologies) and incubated at 37° C. for 16 hours to form colonies. A colony was collected and cultured in Terrific broth (1.2% trypton, 2.4% yeast extract, 17 mM $KH_2PO4$, and 72 mM $K_2HPO_4$; Life Technologies). After culturing the colony, the plasmid was recovered from the E. coli by QIAprep Spin Miniprep Kit (QIAGEN). First, the culture broth (3 to 5 ml) was centrifuged and the supernatant was discarded. The remaining E. coli pellet was suspended with buffer P1 (250 μl). Then, to the suspension was added buffer P2 (250 μl), followed by mixing. Further, after 5 minutes, to the resultant mixture was added buffer N3, followed by mixing. Then, the mixture was centrifuged at 13,000×g for 10 minutes and the supernatant was placed on QIAprep Spin Column. Then, the column was centrifuged at 10,000×g for 30 seconds and a solution was removed from the column. Then, buffer PB (500 μl) was added to the column and a solution was removed from the column by centrifugation. Further, buffer PE (750 μl) was added to the column and a solution was removed from the column by centrifugation. Finally, sterilized water (45 μl) was added to the column, followed by allowing to stand for 1 minute. Then, the column was centrifuged and the eluted DNA was recovered. The direction of the sequence integrated was confirmed by PCR.

The cyclic vector propagated in a large amount was cleaved at a site downstream from the probe with a restriction enzyme HindIII (Takara Shuzo) to form a linear vector. The cleaved DNA was purified by removal of proteins by phenol extraction and precipitation with ethanol.

Then, transcription of the probe sequence was carried out by using T7 promoter. The transcription was carried out by using MAX I script™ In Vitro Transcription Kits (Ambion). Specifically, the probe sequence containing the vector (1 μg) was reacted in 1×transcription buffer containing 0.5 mM dNTP, T7 polymerase (20 U) and a ribonuclease inhibitor (10 U) at 37° C. for 1 hour. After transcription, DNase I (2 U). was added and the mixture was reacted at 37° C. for 15 minutes to remove DNA's. Then, the transcription product was subjected to ethanol precipitation to effect concentration and purification of the reaction product.

Further, a labeled material, biotin-binding psoralen, was attached to the transcription product. This was carried out by using BrightStar™ Psoralen-Biotin Nonisotopic Labeling Kit (Ambion).

Psoralen is a material having an affinity to a nucleic acid and, when it is irradiated with a wavelength of 360 nm, it keeps a stable state with binding to a nucleic acid.

Then, the transcribed RNA (500 ng) was irradiated with a wavelength of 360 nm for 45 minutes. After that, n-butanol saturated with distilled water was added thereto to form a suspension and then n-butanol was removed from the suspension by centrifugation. This operation was repeated twice to remove excess psoralen.

(4) Hybridization of Probe and Transcribed RNA

Hybridization was carried out by using NorthernMax™ (Ambion). Specifically, by using a prehybridization/ hybridization solution warmed to 68° C. beforehand, the membrane prepared in the above (2) was pre-hybridized for more than 30 minutes. Then, the probe prepared in the above (3) was added thereto at a final concentration of 0.1 nM, and hybridization was carried out at 68° C. for 16 hours. After completion of hybridization, the membrane was washed for 10 minutes twice with a low stringency wash solution #1. Then, the membrane was further washed twice for 15 minutes twice with a high stringency wash solution #2 (warmed at 68° C. beforehand).

(5) Detection of Hybridized RNA

Detection of the hybridized RNA was carried out by using BrightStar™ BioDetect™ Nonisotopic DetectionKit (Ambion). Specifically, first, the membrane was washed for 5 minutes twice with 1×wash buffer. Then, the membrane was further washed for 5 minutes twice with the blocking buffer, followed by shaking for 30 minutes. Then, the membrane was further shaken with the blocking buffer containing a streptavidin-alkali phosphatase conjugate for 30 minutes. Since biotin-binding psoralen was attached to the RNA probe, streptavidin was absorbed by the biotin and the streptavidin-alkali phosphatase conjugate was specifically attached to the RNA probe. Then, the membrane was washed for 15 minutes once with the blocking buffer, for 15 minutes 3 times with 1×wash buffer and for 2 minutes twice with 1×assay buffer. Finally, the membrane was allowed to stand at room temperature for 5 minutes with CDP-Star. The membrane was sandwiched in Bio Max cassette (Kodak) together with Bio Max Light Film (Kodak) and exposed to light. The film exposed to light was developed by soaking in a developing solution for 4 minutes, distilled water for 10 seconds and then a fixer for 4 minutes.

Figure 13:
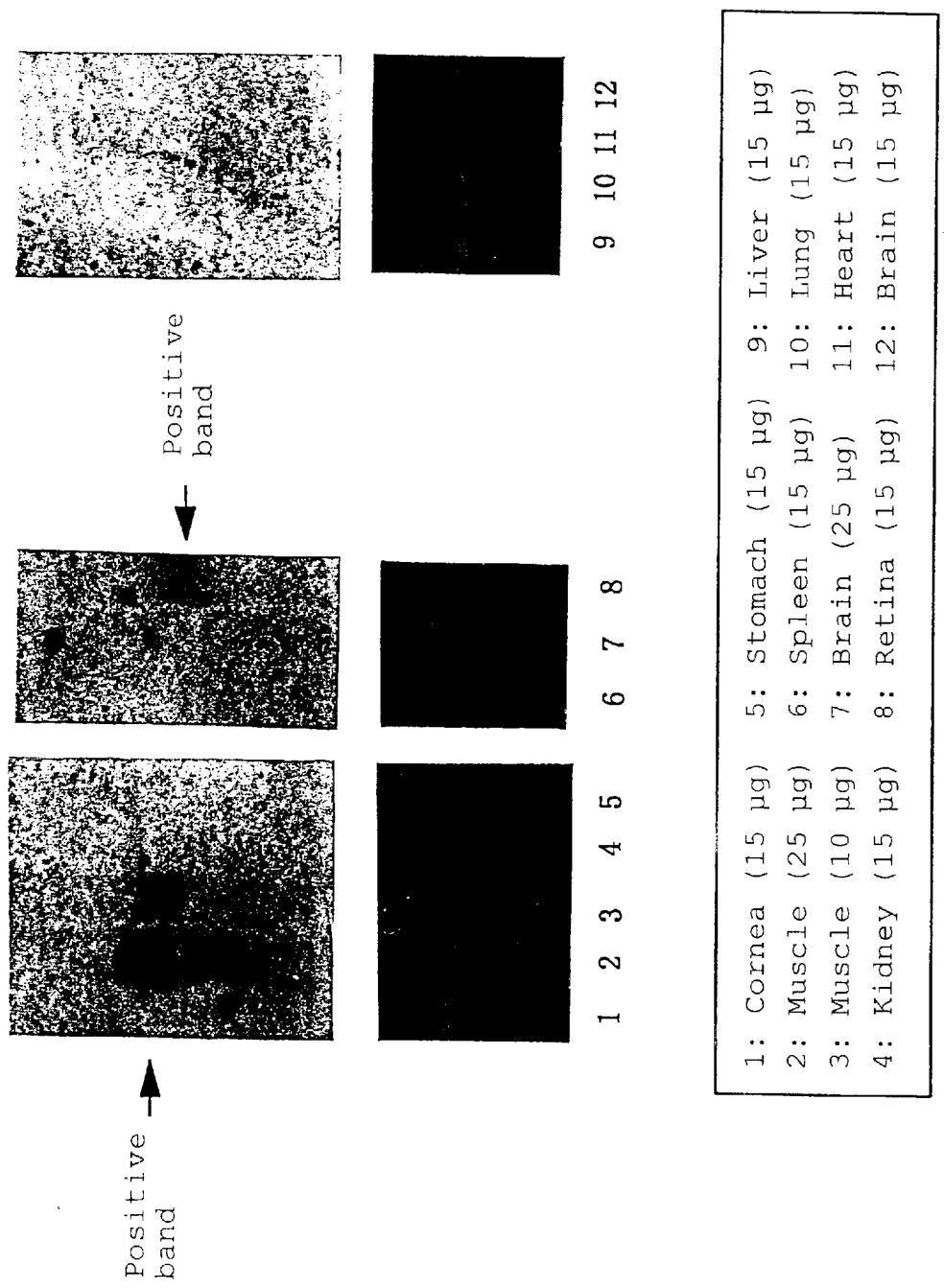
FIG. 13 is a photograph showing results of northern blotting of the Rt88 mRNA obtained in Example 3, hereinafter.

When expression of Rt88 mRNA of rat retinas of various ages was examined, the highest expression amount was recognized in a 6-week old rat. Therefore, retina-specific expression of Rt88 mRNA was examined according to northern blotting technique by using each tissue of a 6-week old rat. As a result, a band was found in the retina and muscle (FIG. 13).

It has been confirmed by using a different probe that the band hybridized to the muscle is skeleton-specific calpain p94, not Rt88. That is, retina-specific expression of Rt88 has been shown by the fact that a band which binds to this probe is detected in the retina.

EXAMPLE 4

Synthesis of Protein

A peptide in which cysteine (Cys) was bound to the peptide of SEQ ID NO: 11 was synthesized according to a solid phase method by using Symphony Multiple Peptide Synthesizer (Protein Technology Inc.) to obtain the peptide as a white powder. Confirmation of the peptide synthesized was carried out by HPLC, mass spectrometry (Kompact MALDI II; Kratos Analystical) and amino acid analysis (System 6300; Beckman).

HPLC

Column: Vydac C18 5μ(inner diameter: 4.8 mm, length: 25 cm; Vydac)

Elution: Eluent A (0.1% trifluoroacetic acid) and Eluent B (acetonitrile containing 0.1% trifluoroacetic acid); Linear gradient elution so that the amount of eluent B was changed from 10% to 40% in 20 minutes.

Flow rate: 1.5 ml/min.

Detection wavelength: 215 nm.

Retention time: about 11 min.

Mass spectrum (M+): Found 2747.0, Theory 2746.1

Amino acid analysis: Arg, 4.77 (5); Asx, 1.95 (2); Cys, 0.34 (1); Glx, 3.97 (4); Gly 2.00 (2); Ile, 0.60 (1); Leu, 0.95 (1); Lys, 0.99 (1); Phe, 1.01 (1); Pro, 1.00 (1); Ser, 0.86 (1); Thr, 0.88 (1); Val, 1.57 (1), wherein the value in the parentheses is the theoretical value. Further, the found values of Cys, Ile and Val are considered to be lower because of hydrolysis.

EXAMPLE 5

Preparation of Polyclonal Antibody

The peptide synthesized in Example 4 was covalently bound to a carrier protein, hemocyanin (KLH), with m-maleinimidobenozyl-N-hydroxysuccinimide ester (MBS). By using this as an antigen, a 10-week old male rabbit (KBL:JW, body weight 2.18 kg) was sensitized by administering a mixture of the antigen (0.50 mg) and complete Freund's adjuvant (CFA) to its back subcutaneously. Further sensitization was carried out on 14 days, 28 days and 42 days after the priming sensitization. Blood samples were collected on 24 days and 38 days after priming sensitization. The above antigen was immobilized on a plate at a concentration of 10 μg/ml and, after blocking, $10^{-1}$ to $10^{-8}$ dilutions of a partial blood of the sensitized rabbit were made and they were reacted with the antigen. After washing, each of them was reacted with an anti-rabbit IgG-POD labeled secondary antibody, followed by washing to measure its titer in terms of color development of a substrate solution ABTS. Purification of the polyclonal antibody was carried out by purifying the IgG fraction from the serum of the immunized rabbit with a carrier for purification of an antibody, HiTrap Protein G (Amershan Pharmacia Biotech), and further by using a polypeptide column.

EXAMPLE 6

Production of Rt88 Recombinant Protein

Preparation of Competent Cells

E. coli M15 (QIAGEN) (10 μl) was added to LB medium (Life Technologies) (2 ml) containing kanamycin (25 μg/ml) and incubated with shaking at 37° C. overnight. This E. coli M15 solution incubated over night (120 μl) was added to LB medium (120 ml) containing kanamycin (25 μg/ml) and incubated with shaking at 37° C. The incubation was continued until $OD_{600}$ became 0.4. When $OD_{600}$ exceeded 0.4, this culture medium containing M15 was transferred to a tube which had been frozen, and allowed to stand in ice for 10 minutes. Then, the culture medium was centrifuged at 4,000×g at 4° C. for 5 minutes and the supernatant was discarded to recover a pellet. This pellet was re-suspended in cold Tris buffer (15 ml, 10 mM Tris, and 50 mM $CaCl_2$) and allowed to stand in ice for more than 2 hours. Further, it was centrifuged at 4,000×g at 4° C. for 5 minutes to remove Tris buffer and suspended in Tris buffer containing glycerol (1 ml, 10 mM Tris, 50 mM $CaCl_2$, and 10% glycerol). Each 50 μl portion thereof was distributed into a tube and stored at −80° C. until it was used.

Preparation of Transformant (Construction of Expression Vector)

A transformant was prepared by using pQE-70 vector contained in QIAexpress Type ATG Kit (QUIAGEN) and M15 based on E. coli K 12 strain. SphI and BamHI restriction sites were provided to 5' and 3' termini of Rt88 cDNA, respectively. Further, primers shown by SEQ ID NOS: 12 and 13 were prepared to delete the original termination codon of Rt88. PCR was carried out by using Rt88 cDNA constructed in pCR2.1 cloning vector (Invitrogen) as the template by using the primer shown by SEQ ID NOS: 12 and 13. RCR cycle of 94° C. for 45 seconds, 60° C. for 45 seconds and then 72° C. for 3 minutes was repeated 35 times. First, the PCR product was constructed in pCR2.1 vector and E. coli was transformed to recover a sufficient amount of a plasmid. Then, the plasmid extracted from E. coli was cleaved with SphI (Life Technologies) and BamHI (Life Technologies) and subjected to electrophoresis on 1% agarose gel to separate cleaved Rt88 cDNA's. The Rt88 cDNA was extracted by GENECLEAN II Kit (BIO 101). Similarly, the expression vector, pQE-70 (QIAGEN) vector, was cleaved with SphI (Life Technologies) and BamHI (Life Technologies)

Rt88 cDNA having SphI and BamHI sites (150 ng) and pQE-70 cleaved with SphI and BamHI (50 ng) were subjected to ligation with T4 ligase (Life Technologies) at 14° C. overnight and used for transformation of the competent cell M15. The resultant transformant was named Escherichia coli K12/M15/Rt88 and have been deposited at National Institute of Bioscience and Human Technology (NIBH), Agency of Industrial Science & Technology, Ministry of International Trade & Industry of 1–3, Higashi 1 chome, Tsukuba-shi, Ibaraki-ken, Japan under the accession number of FERM BP-6622 according to the Budapest treat since Jan. 19, 1999.

Introduction of Expression of Recombinant Protein and Purification of Protein

Figure 15:
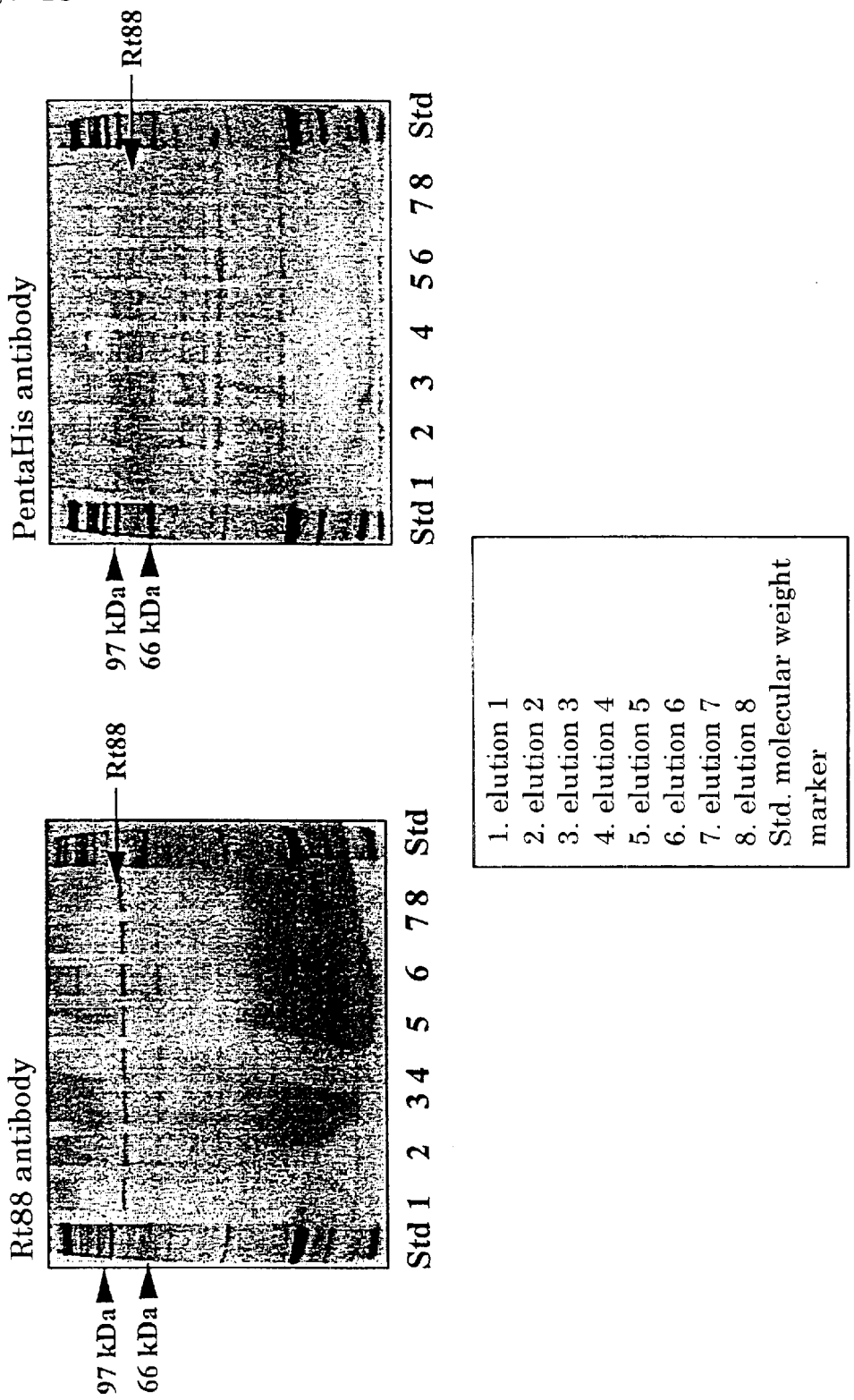
FIG. 15 illustrates electrophoretic migration patterns of Rt88 reacted with the Rt88 antibody obtained in Example 5 hereinafter and PentaHis antibody.

The transformant with pQE-70 vector containing the cDNA was inoculated to LB medium (8 ml) containing kanamycin (25 μg/ml) and ampicillin (100 μg/ml) and incubated at 37° C. overnight. E. coli (7 ml) thus incubated overnight was added to LB medium (200 ml) containing kanamycin (25 μg/ml) and ampicillin (100 μg/ml) and incubated until $OD_{600}$ became to 0.5 to 0.7. When $OD_{600}$ became to 0.5 to 0.7, IPTG was added thereto at a concentration of 1 mM to initiate introduction of expression of a protein. Incubation was ceased 4 hours after initiation of introduction and transferred to a centrifugation tube. The culture medium was centrifuged at 4,000×g at 4° C. for 20 minutes and the supernatant was discarded to recover a pellet. The pellet was disrupted by sonication in Tris buffer (2 ml, Tris-HCl (pH 7.5), 1 mM EDTA, 1 mM EGTA, and 2 mM dithioerythritol) and centrifuged at 10,000×g at 4° C. for 15 minutes to separate into soluble and insoluble proteins. Since Rt88 protein was present in the insoluble protein, the insoluble protein was partly solubilized by 6 M guanidine hydrochloride solution and the guanidine hydrochloride solution was slowly replaced with the above Tris buffer with removing it by a centrifugation tube for dialysis (Ultrafree-CL; Millipore). Since the expressed protein had histidine tag at the C terminus, it was purified by metal chelate affinity chromatography using QIAexpress Type ATG Kit (QUIAGEN). The solvent-replaced solution (4 ml) and 50% NiNTA (1 ml) was mixed with shaking at 4° C. for 60 minutes. This was inserted in a column (QIAexpress Type ATG Kit; QIAGEN) from its upper end and then a solution was allowed to flow out by removing the cap at the lower end. The column was washed twice with a wash buffer (4 ml, 50 mM $NaH_2PO_4$ (pH 8.0), 300 mM NaCl, and 20 mM imidazole) and eluted 8 times with an eluting buffer (0.5 ml, 50 mM $NaH_2PO_4$ (pH 8.0), 300 mM NaCl, and 250 mM imidazole). Purification of the desired protein was confirmed by subjecting the eluted fraction to immunoblotting technique with the Rt88 antibody (polyclonal antibody) prepared in Example 4 and PentaHis antibody (QIAGEN). That is, first, SDS polyacrylamide gel electrophoresis (SDS-PAGE) was carried out in an electrophoresis buffer (25 mM Tris, 192 mM glycine, and 0.1% SDS; pH 8.3) at a constant voltage of 150 V for 90 minutes by using 10% polyacrylamide gel (TEFCO). After electrophoresis, the proteins separated in the gel were transcribed on Immobilon-P membrane (PVDF; Millipore) in an ice-cooled transcription buffer (25 mM Tris, 192 mM glycine, 20% methanol, and 0.1% SDS; pH 8.3) at a constant voltage of 100 V for 70 minutes with a buffer tank type transcription apparatus according to the method described by Towbin et al. (Proc. Natl. Acad. Sci. USA, 76, 4350–4354, 1979). The transcribed membrane was subjected to blocking in Tris buffered physiological saline (TBS, 20 mM Tris-HCl (pH 7.5), and 500 mM sodium chloride) for 30 minutes, followed by washing for 5 minutes twice with TBS containing 0.05% Tween 20 (Bio-Rad) (TTBS). The membrane was incubated with the Rt88 antibody prepared in Example 4 overnight to react the antibody with the proteins on the membrane. Since the expressed protein has histidine tag at the C terminus, by utilizing this, a monoclonal antibody (PentaHis antibody; QIAGEN) having reactivity with 5×His was also used. After completion of the reaction, the membrane was washed for 5 minutes twice with TTBS. Then, the membrane was incubated in a solution of a secondary antibody, alkali phosphatase-labeled goat anti-rabbit IgG (Bio-Rad) for the Rt88 antibody, or alkali phosphatase-labeled goat anti-mouse antibody for PentaHis antibody, diluted 3,000 times with TTBS containing 1% BSA. After completion of the reaction, the membrane was washed for 5 minutes twice with TTBS, and then for 5 minutes twice with TBS. A protein reacted with the Rt88 antibody in the proteins separated on the membrane was detected by using AP Conjugated Substrate Kit (Bio-Rad). Further, the same procedure was repeated by using a transformant with a vector having no inserted gene, i.e., Rt88 gene. As a result, in the protein before purification, no band was detected from the transformant with the vector having no Rt88 gene by the Rt88 antibody, while a band was recognized at about 88 kDa in the insoluble protein from the transformant with the vector containing Rt88 gene by the Rt88 antibody (FIG. 14). In view of this, the protein reactive with Rt88 antibody was confirmed to be that derived from Rt88. Further, the protein containing Rt88 was purified by metal chelate affinity chromatography and Rt88 protein was detected by the antibody according to the same manner as described above. As a result, a single band was recognized at about 88 kDa by the Rt88 antibody. A band was also detected at the same size by PentaHis antibody (FIG. 15). Therefore, expression and purification of Rt88 recombinant protein was confirmed.

EXAMPLE 7

Isolation and Purification of Rt88 From Rat Retina

A 6-week old Sprague-Dawlay rat was slaughtered and the eyes were removed. The retinal tissue was collected in an ice-cooled buffer (20 mM Tris-HCl (pH 7.5), 1 mM EDTA, 1 mM EGTA, 2 mM dithioerythritol, and 0.1 mM leupeptin). The retinal tissue was homogenized in the above buffer in ice by sonication and centrifuged at 13,000×g at 4° C. for 15 minutes to prepare a soluble protein. The concentration of the soluble protein contained in the resultant solution was determined by using BCA protein Assay Kit (PIERCE). A solution containing a predetermined concentration of bovine serum albumin (BSA; Sigma) was used as a standard solution. The retinal soluble protein solution thus determined was dried under reduced pressure, dissolved in a sample buffer (50 mM Tris-HCl (pH 6.8), 8% glycerol, 1.6% sodium dodecyl sulfate (SDS), 4% 2-mercaptoethanol, and 0.002% Boromophenol Blue) and subjected to heat treatment at 100° C. for 5 minutes. The retinal soluble protein (40 μg) was subjected to SDS polyacrylamide gel electrophoresis (SDS-PAGE) according to the method described by Laemmli et al. (Nature 227, 680–685, 1970) in an electrophoresis buffer (25 mM Tris, 192 mM glycine, and 0.1% SDS; pH 8.3) at a constant voltage of 150 V for 90 minutes by using 8% acrylamide gel (TEFCO). After electrophoresis, .according to the above method described by Towbin et al., the proteins separated in the gel was transcribed on Immobilon-P membrane (PVDF; Millipore) in an ice-cooled transcription buffer (25 mM Tris, 192 mM glycine, 20% methanol, and 0.1% SDS; pH 8.3) at a constant voltage of 100 V for 70 minutes by using a buffer tank type transcription apparatus. The transcribed membrane was subjected to blocking in Tris buffered physiological saline (TBS, 20 mM Tris-HCl (pH 7.5), and 500 mM sodium chloride) for 30 minutes. The membrane was washed for 5 minutes twice with TBS containing 0.05% Tween 20 (Bio-Rad) (TTBS) and incubated with the antigen against Rt88 prepared in Example 4 overnight to react it with the proteins on the membrane. After completion of the reaction, the membrane was washed for 5 minutes twice with TTBS and incubated with a solution of alkali phosphatase labeled goat anti-rabbit IgG (Bio-Rad) and diluted 3,000 times with TTBS containing 1% BSA for 1 hour. After completion of the reaction, the membrane was washed for 5 minutes twice with TTBS and then for 5 minutes twice with TBS. Then, a protein reactive with the Rt88 antibody in the retinal soluble protein separated on the membrane with AP Conjugated Substrate Kit (Bio-Rad). As a result, a protein which were considered to be Rt88 of a molecular weight of about 90 kDa was detected.

The resultant retinal soluble protein solution was fractionated by HPLC with an anion exchange resin TSKgel DEAE-5PW (Tosoh). The protein solution (20 mg) was fractionated by developing the protein solution with the above buffer at a flow rate of 1 ml/minute to absorb the protein on the resin, eluting the absorbed protein with the buffer by increasing its sodium chloride concentration from 0 mM to 500 mM linearly to separate the protein. All the fractions thus separated were activated and the casein decomposing activity detected by zymography technique. Each fraction (1,000 μl) was concentrated (to 100 μl) and the concentrate (20 μl), as a protein solution, was dissolved in a sample buffer (50 mM Tris-HCl (pH 6.8), 8% glycerol, 4% 2-mercaptoethanol, and 0.002% Bromophenol Blue) under non-denaturation reducing conditions and separated by electrophoresis using 7% acrylamide gel (TEFCO) containing 0.1% casein in ice at a constant voltage of 125 V for 150 minutes. As an electrophoresis buffer, 25 mM Tris and 192 mM glycine (pH 8.3) were used. After separation, the gel was incubated in a buffer containing calcium (20 mM Tris-HCl (pH 7.4), 1 mM calcium chloride, and 10 mM dithiothreitol) for 20 hours to activate the calcium dependent protease in the gel. The incubated gel was stained with 0.05% Coomassie Brilliant Blue R-250 (Bio-Rad) (10% acetic acid and 40% methanol) and the protease activity was detected as casein decomposition activity. As a result, casein decomposing activity was detected in some fractions. Further, these fractions having casein decomposing activity were subjected to SDS-PAGE and transcription on the membrane according to the same manner as described above to examine the reactivity with the Rt88 antibody prepared in Example 4. As a result, a reactive fraction was obtained at about molecular weight of about 90 kDa.

EXAMPLE 8

Rt88 Gene Transfer

The process for construction of a vector is roughly divided into the following eight steps. (1) Extraction of total RNA and treatment with DNase I; (2) RT-PCR for amplification of Rt88 cDNA; (3) Integration into a plasmid and transformation of *E. coli*; (4) Purification of the plasmid; (5) Cleavage of Rt88 sequence from the plasmid and cut out from the gel; (6) Cleavage of vector pRc/CMV and dephosphorylation treatment for expression in human 293 cells; (7) Integration of the sequence cut out in the above step (5) into the vector dephosphorylated in the above step (6); and (8) Purification of the plasmid and confirmation of the orientation. Details are as follows.

(1) According to the same manner as that described in Example 1 (1), extraction of a total RNA and DNase treatment were carried out by using a 6-week old Sprague-Dawley male rat.

(2) The DNase I-treated total RNA was subjected to a reverse transcription reaction with oligo dT primer under conditions of 42° C. for 50 minutes and 70° C. for 15 minutes. Then, the resultant cDNA was amplified by repeating a PCR cycle of 94° C. for 1 minute, 53° C. for 1 minute and then 72° C. for 3 minutes, 35 times.

(3) According to the same manner as that described in Example 1 (2), integration into a plasmid and transformation of *E. coli* were carried out.

(4) According to the same manner as that described in Example 1 (2), the plasmid was purified.

(5) pCR 2.1 (INVITROGEN) containing Rt88 cDNA was cleaved with restriction enzyme BstXI (Takara Shuzo) to extract only the cDNA of Rt88. Electrophoresis was carried out using 1% agarose gel and the band of Rt88 cDNA was cut out of the gel. Then, Rt88 cDNA was recovered from the gel by using EASYRAP™ Ver. 2 (Takara Shuzo). Further, ethanol precipitation was carried out to concentrate it.

(6) Vector pRc/CMV (Invitrogen) for expression in 293 cells derived from human fetal kidney was also cleaved with restriction enzyme BstXI (Takara Shuzo). According to the same manner as that described in the above (5), the vector was recovered-from the gel. The vector was further dephosphorylated. Specifically, the vector (2 μg) and calf intestin alkali phosphatase (CIAP; 120 U; STRATAGENE) were reacted in 1×buffer (50 mM Tris-HCl (pH 8.0), 0.1 mM EDTA) at 37° C. for 15 minutes and 50° C. for 15 minutes. After completion of the reaction, purification and concentration were carried out by phenol treatment and ethanol precipitation.

(7) According to the same manner as described in the above Example 1 (2), Rt88 was integrated into the vector obtained in the above (6) and used for transformation.

(8) According to the same manner as described in the above Example 1 (2), the plasmid was purified from the resultant transformant. The orientation of Rt88 integrated in the plasmid was confirmed by cleavage with restriction enzyme KpnI (Takara Shuzo), followed by electrophoresis.

Gene Transfer

Figure 16:
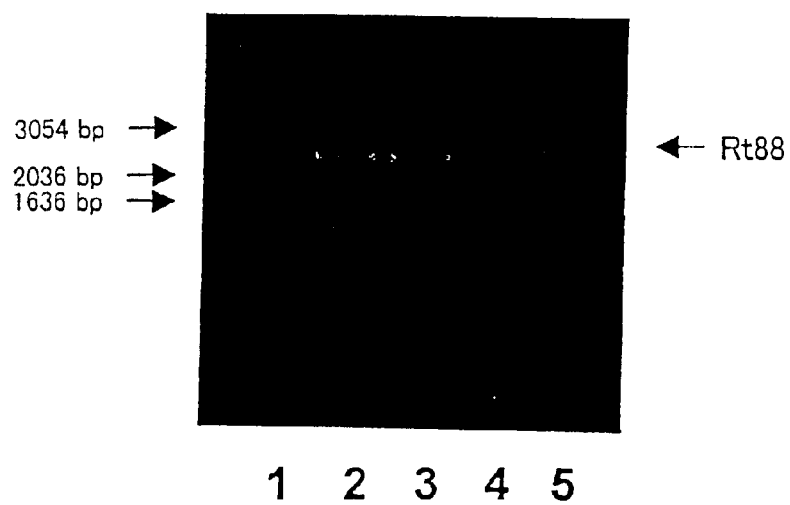
FIG. 16 is a photograph showing electrophoretic migration patterns of the PCR products in Example 7 hereinafter.

293 Cells derived from human fetal kidney were sub-cultured in a cell culture dish of 6 cm diameter at a concentration of 50%, 24 hours prior to gene transfer. Lipofectin reagent (10 μl, Life Technologies) was dissolved in OPTI-MEM I medium (200 μl) and allowed to stand at room temperature for 45 minutes to obtain Solution A. On the other hand, an expression vector DNA (2 μg) was dissolved in OPTI-MEM I (200 μl) to obtain Solution B. Solutions A and B were mixed and allowed to stand at room temperature for 15 minutes. The cells in the 6 cm dish was washed with serum-free Dulbecco modified MEM medium and to this were added the mixture of Solutions A and B and OPTI-MEM I medium (1.6 ml), followed by incubation at 37° C. for 6 hours in a 5% $CO_2$ incubator. The medium was removed and Dulbecco modified MEM medium containing 10% fetal bovine serum (4 ml) was added. The cells were incubated at 37° C. for 48 hours in a 5% $CO_2$ incubator. The cells were diluted 1:5 in a 10 cm dish, sub-cultured and cultured in Dulbecco modified MEM medium containing G418 (400 μg/ml; GENETICIN; Life Technologies) and 10% fetal bovine serum so that only the gene transferred cells survived. Selection of the cells was continued until only the transformed cells were remained. Then, the cells were sub-cultured in a 6 cm cell culture dish and cultured in Dulbecco modified MEM medium containing G418 (200 μg/ml) and 10% fetal bovine serum. When the cells reached confluent growth, the medium was removed and the cells were washed twice with a phosphate buffer, followed by addition of TRIzol reagent (1 ml; Life Technologies) and standing at room temperature for 10 minutes. The cells were transferred to a homogenizer and homogenized. Then, the homogenate was transferred to a 1.5 ml tube. Chloroform (0.2 ml) was added thereto and mixed. The mixture was allowed to stand at room temperature for 3 minutes and centrifuged at 12,000×g at 4° C. for 15 minutes to recover an aqueous layer. To this layer was added 2-isopropanol (0.5 ml) and mixed. The mixture was allowed to stand at room temperature for 10 minutes and centrifuged at 12,000×g at 4° C. for 10 minutes. The resultant precipitate was suspended in 75% ethanol (1 ml) and further centrifuged at 12,000×g at 4° C. for 5 minutes to recover the precipitate. This precipitate was dissolved in an appropriate amount of water. Then, it was treated with DNase I (Life Technologies) to obtain a total RNA. The total RNA was subjected to a reverse transcription reaction with oligo dT primer (Life Technologies) at 42° C. for 50 minutes and 70° C. for 15 minutes. The resultant cDNA was amplified by repeating a PCR cycle of 94° C. for 1 minute, 58° C. for 1 minute and then 72° C. for 3 minutes, 35 times using GSP's of SEQ ID NOS: 4 and 8. The PCR reaction was carried out in a reaction mixture (50 μl) containing 20 mM Tris-HCl, 50 mM KCl, 0.2 mM dNTP, 2 mM MgCl2, 2.5U Taq DNA polymerase and 0.2 μM primers. The PCR product was subjected to electrophoresis using 1.2% agarose gel in TAE buffer (Life Technologies) at 75 V for about 1 hour. As a result, a band of the amplified cDNA was recognized at the expected size (FIG. 16). On the other hand, no amplification was observed in 293 cells which did not contain Rt88 gene, i.e., contained only the vector. Therefore, it has been shown that Rt88 mRNA is expressed in 293 cells to which Rt88 gene was transferred and normal transcription is taken place in the gene transferred cells.

SEQUENCE LISTING FREE TEXT

SEQ ID NO: 2 is cDNA (61–1240)/mRNA. SEQ ID NO: 3 to SEQ ID NO: 10 and SEQ ID NO: 12 to SEQ ID NO: 12 are primers. SEQ ID NO: 11 is an antigen.

What is claimed is:

1. A protein comprising an amino acid sequence according to SEQ ID No:.1.

2. The protein according to claim 1 which is calpain.

3. The protein according to claim 2 which is of the retina origin.

4. A peptide having an amino acid sequence according to SEQ ID No: 14.

5. A process for producing the protein according to claim 1, which comprises culturing in a culture medium a transformant transformed with a vector comprising a DNA encoding the protein according to claim 1, and producing and accumulating the protein according to claim 1 in the culture.

* * * * *

SEQUENCE LISTING

<160> NUMBER OF SEQ ID NOS: 16

<210> SEQ ID NO 1
<211> LENGTH: 757
<212> TYPE: PRT
<213> ORGANISM: Sprague-Dawley rat

<400> SEQUENCE: 1

```
Met Pro Tyr Leu Leu Pro Gly Phe Phe Cys Asp Arg Val Ile Arg Glu
 1               5                  10                  15

Arg Asp Arg Arg Asn Gly Glu Gly Thr Val Ser Gln Pro Leu Lys Phe
                20                  25                  30

Glu Gly Gln Asp Phe Val Val Leu Lys Gln Arg Cys Leu Ala Gln Lys
            35                  40                  45

Cys Leu Phe Glu Asp Arg Val Phe Pro Ala Gly Thr Gln Ala Leu Gly
        50                  55                  60

Ser His Glu Leu Ser Gln Lys Ala Lys Met Lys Ala Ile Thr Trp Lys
    65                  70                  75                  80

Arg Pro Lys Glu Ile Cys Glu Asn Pro Arg Phe Ile Ile Gly Gly Ala
                85                  90                  95

Asn Arg Thr Asp Ile Cys Gln Gly Asp Leu Gly Asp Cys Trp Phe Leu
            100                 105                 110

Ala Ala Ile Ala Cys Leu Thr Leu Asn Glu Arg Leu Leu Phe Arg Val
        115                 120                 125

Ile Pro His Asp Gln Ser Phe Thr Glu Asn Tyr Ala Gly Ile Phe His
    130                 135                 140

Phe Gln Phe Trp Arg Tyr Gly Asp Trp Val Asp Val Val Ile Asp Asp
145                 150                 155                 160

Cys Leu Pro Thr Tyr Asn Asn Gln Leu Val Phe Thr Lys Ser Asn His
                165                 170                 175

Arg Asn Glu Phe Trp Ser Ala Leu Leu Glu Lys Ala Tyr Ala Lys Leu
            180                 185                 190

His Gly Ser Tyr Glu Ala Leu Lys Gly Gly Asn Thr Thr Glu Ala Met
        195                 200                 205

Glu Asp Phe Thr Gly Gly Val Thr Glu Phe Phe Glu Ile Lys Asp Ala
    210                 215                 220

Pro Ser Asp Met Tyr Lys Ile Met Arg Lys Ala Ile Glu Arg Gly Ser
225                 230                 235                 240

Leu Met Gly Cys Ser Ile Asp Asp Gly Thr Asn Met Thr Tyr Gly Thr
                245                 250                 255

Ser Pro Ser Gly Leu Asn Met Gly Glu Leu Ile Ala Arg Met Val Arg
            260                 265                 270

Asn Met Asp Asn Ser Leu Leu Arg Asp Ser Asp Leu Asp Pro Arg Ala
        275                 280                 285

Ser Asp Asp Arg Pro Ser Arg Thr Ile Val Pro Val Gln Tyr Glu Thr
    290                 295                 300
```

```
Arg Met Ala Cys Gly Leu Val Lys Gly His Ala Tyr Ser Val Thr Gly
305                 310                 315                 320

Leu Glu Glu Ala Leu Phe Lys Gly Glu Lys Val Lys Leu Val Arg Leu
                325                 330                 335

Arg Asn Pro Trp Gly Gln Val Glu Trp Asn Gly Ser Trp Ser Asp Gly
            340                 345                 350

Trp Lys Asp Trp Ser Phe Val Asp Lys Asp Glu Lys Ala Arg Leu Gln
                355                 360                 365

His Gln Val Thr Glu Asp Gly Glu Phe Trp Met Ser Tyr Asp Asp Phe
        370                 375                 380

Val Tyr His Phe Thr Lys Leu Glu Ile Cys Asn Leu Thr Ala Asp Ala
385                 390                 395                 400

Leu Glu Ser Asp Lys Leu Gln Thr Trp Thr Val Ser Val Asn Glu Gly
                405                 410                 415

Arg Trp Val Arg Gly Cys Ser Ala Gly Gly Cys Arg Asn Phe Pro Asp
            420                 425                 430

Thr Phe Trp Thr Asn Pro Gln Tyr Arg Leu Lys Leu Leu Glu Glu Asp
                435                 440                 445

Asp Asp Pro Asp Asp Ser Glu Val Ile Cys Ser Phe Leu Val Ala Leu
        450                 455                 460

Met Gln Lys Asn Arg Arg Lys Asp Arg Lys Leu Gly Ala Asn Leu Phe
465                 470                 475                 480

Thr Ile Gly Phe Ala Ile Tyr Glu Val Pro Lys Glu Met His Gly Asn
                485                 490                 495

Lys Gln His Leu Gln Lys Asp Phe Phe Leu Tyr Asn Ala Ser Lys Ala
            500                 505                 510

Arg Ser Lys Thr Tyr Ile Asn Met Arg Glu Val Ser Gln Arg Phe Arg
            515                 520                 525

Leu Pro Pro Ser Glu Tyr Val Ile Val Pro Ser Thr Tyr Glu Pro His
        530                 535                 540

Gln Glu Gly Glu Phe Ile Leu Arg Val Phe Ser Glu Lys Arg Asn Leu
545                 550                 555                 560

Ser Glu Glu Ala Glu Asn Thr Ile Ser Val Asp Arg Pro Val Pro Arg
                565                 570                 575

Pro Gly His Thr Asp Gln Glu Ser Glu Glu Gln Gln Phe Arg Asn
            580                 585                 590

Ile Phe Arg Gln Ile Ala Gly Asp Asp Met Glu Ile Cys Ala Asp Glu
            595                 600                 605

Leu Lys Asn Val Leu Asn Thr Val Val Asn Lys His Lys Asp Leu Lys
        610                 615                 620

Thr Gln Gly Phe Thr Leu Glu Ser Cys Arg Ser Met Ile Ala Leu Met
625                 630                 635                 640

Asp Thr Asp GLy Ser Gly Arg Leu Asn Leu Gln Glu Phe His His Leu
                645                 650                 655

Trp Lys Lys Ile Lys Ala Trp Gln Lys Ile Phe Lys His Tyr Asp Thr
            660                 665                 670

Asp His Ser Gly Thr Ile Asn Ser Tyr Glu Met Arg Asn Ala Val Asn
        675                 680                 685

Asp Ala Gly Phe His Leu Asn Ser Gln Leu Tyr Asp Ile Ile Thr Met
        690                 695                 700

Arg Tyr Ala Asp Lys His Met Asn Ile Asp Phe Asp Ser Phe Ile Cys
705                 710                 715                 720
```

Cys Phe Val Arg Leu Glu Gly Met Phe Arg Ala Phe His Ala Phe Asp
        725                 730                 735

Lys Asp Gly Asp Gly Ile Ile Lys Leu Asn Val Leu Glu Trp Leu Gln
        740                 745                 750

Leu Thr Met Tyr Ala
        755

<210> SEQ ID NO 2
<211> LENGTH: 2353
<212> TYPE: DNA
<213> ORGANISM: Sprague-Dawley rat
<220> FEATURE:
<223> OTHER INFORMATION: cDNA (61-1240)/mRNA

<400> SEQUENCE: 2

| | | |
|---|---|---|
| tcaggcctgg gctgagggtg cagcaggaga ggccgcaggg aaggccgggt tccactgctc | 60 |
| gtcatc atg ccc tac ctg ctg ccg gga ttc ttc tgt gac aga gtg atc | 108 |
| aga gaa agg gac agg aga aat gga gag ggc acc gtc tca cag cct ctc | 156 |
| aag ttt gag ggg cag gat ttt gtc gtt ctc aaa caa cgg tgt ctg gct | 204 |
| cag aag tgc ctc ttt gaa gat cga gtc ttc cca gca ggt aca cag gcc | 252 |
| ctt ggc tca cat gag ctg agc cag aaa gcc aag atg aag gcc atc act | 300 |
| tgg aag agg cca aag gaa att tgt gag aat ccc cga ttt atc att ggt | 348 |
| gga gcc aac agg act gac atc tgc caa gga gat cta ggg gac tgc tgg | 396 |
| ttt ctt gca gcc att gcc tgt ctg acc ctg aat gag cga ctg ctt ttc | 444 |
| cga gtt ata cct cat gat caa agt ttc act gaa aac tac gca ggg atc | 492 |
| ttc cac ttc cag ttc tgg cgc tat gga gac tgg gta gat gtg gtt att | 540 |
| gac gac tgt ctg ccg aca tac aac aac cag ctg gtc ttc acc aaa tcc | 588 |
| aac cac cgc aat gag ttc tgg agt gct cta ctg gag aaa gca tat gcc | 636 |
| aag ctc cat ggt tcc tat gaa gct ctg aaa ggt ggg aac acc aca gaa | 684 |
| gcc atg gag gac ttc aca gga ggg gtg aca gag ttt ttt gag atc aag | 732 |
| gat gct ccg agt gac atg tac aag atc atg agg aaa gct atc gag aga | 780 |
| ggc tcc ctc atg ggc tgc tcc att gat gat ggc acc aac atg act tat | 828 |
| gga acc tct cct tct ggt ctg aac atg ggg gaa ttg att gcg cgg atg | 876 |
| gtg aga aat atg gat aac tcg ctg ctc aga gac tca gac ctg gac ccc | 924 |
| agg gcc tca gat gac aga ccg tca cgg aca att gtt ccg gtg cag tat | 972 |
| gaa aca aga atg gcc tgt gga ctg gtg aaa ggg cac gcc tat tca gtc | 1020 |
| act ggg ctg gag gag gcc ctg ttc aaa ggc gag aag gtg aag ctg gtg | 1068 |
| cgg ctg cgg aac ccc tgg ggc cag gtg gag tgg aac ggc tct tgg agt | 1116 |
| gat ggt tgg aag gac tgg agc ttt gtg gac aaa gac gag aag gcc cgt | 1164 |
| ctg cag cac cag gtc acc gag gat gga gag ttc tgg atg tca tat gat | 1212 |
| gac ttt gtc tac cat ttc aca aag ctg gag atc tgc aac ctc aca gct | 1260 |
| gat gcc ctg gag tcc gat aag ctt cag acc tgg aca gtg tct gta aat | 1308 |
| gag ggc cgc tgg gtg agg ggc tgt tct gct gga ggc tgc cgg aac ttc | 1356 |
| cca gac act ttc tgg acc aac ccg cag tac cgt ctc aag ctc ctg gag | 1404 |
| gag gat gat gac cct gat gac tct gag gtg att tgc agc ttc ctc gtg | 1452 |

-continued

```
gct ctg atg cag aaa aat cgg cgc aag gac cgg aag ctg ggg gcc aac      1500
ctc ttc acc att ggc ttc gct atc tac gag gtt ccc aaa gag atg cac      1548
ggg aat aag caa cac ctg cag aag gac ttc ttc ttg tac aat gcc tcc      1596
aag gcc agg agc aaa acc tac atc aac atg cgg gag gtg tcc cag cgc      1644
ttc cgc ctg ccg ccc agc gag tat gtc att gtc ccc tcc act tac gag      1692
ccc cat cag gag ggg gaa ttc atc ctc cgg gtc ttc tct gaa aag agg      1740
aat ctc tct gag gaa gct gag aat aca atc tct gtg gac cgg cca gtg      1788
cca cgg cct ggc cac aca gac cag gag agt gag gag cag cag caa ttc      1836
cgg aac atc ttc agg cag att gca ggc gac gac atg gag atc tgt gcg      1884
gat gaa ctc aag aat gtc ctt aat acg gtg gtg aac aaa cac aag gac      1932
ctg aag aca caa ggg ttc act ctg gag tcc tgc aga agc atg ata gct      1980
ctc atg gat aca gat ggc tct ggg aga ctg aat ctt caa gag ttc cat      2028
cac ctc tgg aaa aag atc aag gcc tgg cag aaa atc ttc aaa cac tat      2076
gac act gac cat tct ggt acc atc aat agc tat gag atg cga aat gca      2124
gtc aat gat gca ggc ttc cat ctc aac agc caa ctc tat gac atc atc      2172
acc atg cgc tac gca gac aaa cac atg aac atc gac ttt gac agc ttc      2220
atc tgc tgc ttc gtc agg ctg gaa ggg atg ttc aga gct ttt cac gca      2268
ttt gac aag gat gga gat ggc atc atc aaa ctg aac gta ctt gag tgg      2316
ctg cag ctt acc atg tat gcc tga                                      2340
accagatgac ctc                                                       2353
```

<210> SEQ ID NO 3
<211> LENGTH: 30
<212> TYPE: DNA
<213> ORGANISM: Artificial Sequence
<220> FEATURE:
<223> OTHER INFORMATION: primer

<400> SEQUENCE: 3
cttccaaagt tgcctgccat gccgaccgtt                              30

<210> SEQ ID NO 4
<211> LENGTH: 30
<212> TYPE: DNA
<213> ORGANISM: Artificial Sequence
<220> FEATURE:
<223> OTHER INFORMATION: primer

<400> SEQUENCE: 4
gaggtcatct ggttcaggca tacatggtaa                              30

<210> SEQ ID NO 5
<211> LENGTH: 26
<212> TYPE: DNA
<213> ORGANISM: Artificial Sequence
<220> FEATURE:
<223> OTHER INFORMATION: primer

<400> SEQUENCE: 5
ggtgacagag tttttgaga tcaagg                                   26

<210> SEQ ID NO 6
<211> LENGTH: 30

```
<212> TYPE: DNA
<213> ORGANISM: Artificial Sequence
<220> FEATURE:
<223> OTHER INFORMATION: primer

<400> SEQUENCE: 6
gatctccagc tttgtgaaat ggtagacaaa                                30

<210> SEQ ID NO 7
<211> LENGTH: 30
<212> TYPE: DNA
<213> ORGANISM: Artificial Sequence
<220> FEATURE:
<223> OTHER INFORMATION: primer

<400> SEQUENCE: 7
tgagcagcga gttatccata tttctcacca                                30

<210> SEQ ID NO 8
<211> LENGTH: 30
<212> TYPE: DNA
<213> ORGANISM: Artificial Sequence
<220> FEATURE:
<223> OTHER INFORMATION: primer

<400> SEQUENCE: 8
tcatcatgcc ctacctgctg ccgggattct                                30

<210> SEQ ID NO 9
<211> LENGTH: 30
<212> TYPE: DNA
<213> ORGANISM: Artificial Sequence
<220> FEATURE:
<223> OTHER INFORMATION: primer

<400> SEQUENCE: 9
gatgaaggcc atcacttgga agaggccaaa                                30

<210> SEQ ID NO 10
<211> LENGTH: 30
<212> TYPE: DNA
<213> ORGANISM: Artificial Sequence
<220> FEATURE:
<223> OTHER INFORMATION: primer

<400> SEQUENCE: 10
agaggttcca taagtcatgt tggtgccatc                                30

<210> SEQ ID NO 11
<211> LENGTH: 22
<212> TYPE: PRT
<213> ORGANISM: Artificial Sequence
<220> FEATURE:
<223> OTHER INFORMATION: antigen

<400> SEQUENCE: 11

Arg Val Ile Arg Glu Arg Asp Arg Arg Asn Gly Glu Gly Thr Val Ser
                 5                  10                  15

Gln Pro Leu Lys Phe Glu
            20

<210> SEQ ID NO 12
<211> LENGTH: 23
<212> TYPE: DNA
<213> ORGANISM: Artificial Sequence
<220> FEATURE:
```

<223> OTHER INFORMATION: primer

<400> SEQUENCE: 12
ctgctcgtca gcatgcccta cct      23

<210> SEQ ID NO 13
<211> LENGTH: 26
<212> TYPE: DNA
<213> ORGANISM: Artificial Sequence
<220> FEATURE:
<223> OTHER INFORMATION: primer

<400> SEQUENCE: 13
gtcatctggt ggatccatac atggta      26

<210> SEQ ID NO 14
<211> LENGTH: 23
<212> TYPE: PRT
<213> ORGANISM: Artificial Sequence
<220> FEATURE:
<223> OTHER INFORMATION: antigen

<400> SEQUENCE: 14

Cys Arg Val Ile Arg Glu Arg Asp Arg Arg Asn Gly Glu Gly Thr Val Ser
1               5                   10                  15

Gln Pro Leu Lys Phe Glu
            20

<210> SEQ ID NO 15
<211> LENGTH: 821
<212> TYPE: PRT
<213> ORGANISM: Norway rat
<220> FEATURE:
<223> OTHER INFORMATION: p94 protein

<400> SEQUENCE: 15

Met Pro Thr Val Ile Ser Pro Thr Val Ala Pro Arg Thr Gly Ala Glu
1               5                   10                  15

Pro Arg Ser Pro Gly Pro Val Pro His Pro Ala Gln Gly Lys Thr Thr
            20                  25                  30

Glu Ala Gly Gly Gly His Pro Gly Gly Ile Tyr Ser Ala Ile Ile Ser
        35                  40                  45

Arg Asn Phe Pro Ile Ile Gly Val Lys Glu Lys Thr Phe Glu Gln Leu
    50                  55                  60

His Lys Lys Cys Leu Glu Lys Lys Val Leu Tyr Leu Asp Pro Glu Phe
65                  70                  75                  80

Pro Pro Asp Glu Thr Ser Leu Phe Tyr Ser Gln Lys Phe Pro Ile Gln
                85                  90                  95

Phe Val Trp Lys Arg Pro Pro Glu Ile Cys Glu Asn Pro Arg Phe Ile
            100                 105                 110

Ile Gly Gly Ala Asn Arg Thr Asp Ile Cys Gln Gly Asp Leu Gly Asp
        115                 120                 125

Cys Trp Leu Leu Ala Ala Ile Ala Cys Leu Thr Leu Asn Glu Arg Leu
    130                 135                 140

Leu Phe Arg Val Ile Pro His Asp Gln Ser Phe Thr Glu Asn Tyr Ala
145                 150                 155                 160

Gly Ile Phe His Phe Gln Phe Trp Arg Tyr Gly Asp Trp Val Asp Val
                165                 170                 175

Val Ile Asp Asp Cys Leu Pro Thr Tyr Asn Asn Gln Leu Val Phe Thr
            180                 185                 190

```
Lys Ser Asn His Arg Asn Glu Phe Trp Ser Ala Leu Leu Glu Lys Ala
        195                 200                 205
Tyr Ala Lys Leu His Gly Ser Tyr Glu Ala Leu Lys Gly Gly Asn Thr
        210                 215                 220
Thr Glu Ala Met Glu Asp Phe Thr Gly Val Thr Glu Phe Phe Glu
225                 230                 235                 240
Ile Lys Asp Ala Pro Ser Asp Met Tyr Lys Ile Met Arg Lys Ala Ile
                245                 250                 255
Glu Arg Gly Ser Leu Met Gly Cys Ser Ile Asp Asp Gly Thr Asn Met
            260                 265                 270
Thr Tyr Gly Thr Ser Pro Ser Gly Leu Asn Met Gly Glu Leu Ile Ala
        275                 280                 285
Arg Met Val Arg Asn Met Asp Asn Ser Leu Leu Arg Asp Ser Asp Leu
290                 295                 300
Asp Pro Arg Ala Ser Asp Asp Arg Pro Ser Arg Thr Ile Val Pro Val
305                 310                 315                 320
Gln Tyr Glu Thr Arg Met Ala Cys Gly Leu Val Lys Gly His Ala Tyr
                325                 330                 335
Ser Val Thr Gly Leu Glu Glu Ala Leu Phe Lys Gly Glu Lys Val Lys
            340                 345                 350
Leu Val Arg Leu Arg Asn Pro Trp Gly Gln Val Glu Trp Asn Gly Ser
        355                 360                 365
Trp Ser Asp Gly Trp Lys Asp Trp Ser Phe Val Asp Lys Asp Glu Lys
        370                 375                 380
Ala Arg Leu Gln His Gln Val Thr Glu Asp Gly Glu Phe Trp Met Ser
385                 390                 395                 400
Tyr Asp Asp Phe Val Tyr His Phe Thr Lys Leu Glu Ile Cys Asn Leu
                405                 410                 415
Thr Ala Asp Ala Leu Gln Ser Asp Lys Leu Gln Thr Trp Thr Val Ser
            420                 425                 430
Val Asn Glu Gly Arg Trp Val Arg Gly Cys Ser Ala Gly Gly Cys Arg
        435                 440                 445
Asn Phe Pro Asp Thr Phe Trp Thr Asn Pro Gln Tyr Arg Leu Lys Leu
        450                 455                 460
Leu Glu Glu Asp Asp Asp Pro Asp Asp Ser Glu Val Ile Cys Ser Phe
465                 470                 475                 480
Leu Val Ala Leu Met Gln Lys Asn Arg Arg Lys Asp Arg Lys Leu Gly
                485                 490                 495
Ala Asn Leu Phe Thr Ile Gly Phe Ala Ile Tyr Glu Val Pro Lys Glu
            500                 505                 510
Met His Gly Asn Lys Gln His Leu Gln Lys Asp Phe Phe Leu Tyr Asn
        515                 520                 525
Ala Ser Lys Ala Arg Ser Lys Thr Tyr Ile Asn Met Arg Glu Val Ser
        530                 535                 540
Gln Arg Phe Arg Leu Pro Pro Ser Glu Tyr Val Ile Val Pro Ser Thr
545                 550                 555                 560
Tyr Glu Pro His Gln Glu Gly Glu Phe Ile Leu Arg Val Phe Ser Glu
                565                 570                 575
Lys Arg Asn Leu Ser Glu Glu Ala Glu Asn Thr Ile Ser Val Asp Arg
            580                 585                 590
Pro Val Lys Lys Lys Asn Lys Pro Ile Ile Phe Val Ser Asp Arg
        595                 600                 605
```

```
Ala Asn Ser Asn Lys Glu Leu Gly Val Asp Gln Glu Ala Glu Glu Gly
        610                 615                 620
Lys Asp Lys Thr Gly Pro Asp Lys Gln Gly Glu Ser Pro Gln Pro Arg
625                 630                 635                 640
Pro Gly His Thr Asp Gln Glu Ser Glu Glu Gln Gln Phe Arg Asn
                645                 650                 655
Ile Phe Arg Gln Ile Ala Gly Asp Asp Met Glu Ile Cys Ala Asp Glu
            660                 665                 670
Leu Lys Asn Val Leu Asn Thr Val Asn Lys His Lys Asp Leu Lys
        675                 680                 685
Thr Gln Gly Phe Thr Leu Glu Ser Cys Arg Ser Met Ile Ala Leu Met
        690                 695                 700
Asp Thr Asp Gly Ser Gly Arg Leu Asn Leu Gln Glu Phe His His Leu
705                 710                 715                 720
Trp Lys Lys Ile Lys Ala Trp Gln Lys Ile Phe Lys His Tyr Asp Thr
                725                 730                 735
Asp His Ser Gly Thr Ile Asn Ser Tyr Glu Met Arg Asn Ala Val Asn
            740                 745                 750
Asp Ala Gly Phe His Leu Asn Ser Gln Leu Tyr Asp Ile Ile Thr Met
        755                 760                 765
Arg Tyr Ala Asp Lys His Met Asn Ile Asp Phe Asp Ser Phe Ile Cys
770                 775                 780
Cys Phe Val Arg Leu Glu Gly Met Phe Arg Ala Phe His Ala Phe Asp
785                 790                 795                 800
Lys Asp Gly Asp Gly Ile Ile Lys Leu Asn Val Leu Glu Trp Leu Gln
                805                 810                 815
Leu Thr Met Tyr Ala
            820
```

<210> SEQ ID NO 16
<211> LENGTH: 3138
<212> TYPE: DNA
<213> ORGANISM: Norway rat
<220> FEATURE:
<223> OTHER INFORMATION: DNA encoding p94 protein

<400> SEQUENCE: 16

```
ttttcttttt tcctctggc  aagcctgctg ctggtaggca cccccaggta gaagctgcgt      60
ctaaatcctt tattgcctct tcctcaggaa tacctattgc tctagggtca tagttccacct   120
atttaagctg gtcagaggcc agccaatttt ctgataggat ttaaactttg aagagactgt   180
agccattttt ttcctcagat gacagaatca cttcaacttc cactttgtaa tcgcttcctt   240
tccttgaagg tagctgaatc ttgttttctt taaaaacgtc ttccttccaa agttgcctgc   300
catgccgacc gttattagtc caactgtggc cccaaggaca ggagctgagc ccaggtcccc   360
agggccagtt cctcacccag ctcaaggcaa gaccactgag gctggaggtg acacccggg    420
tggcatctat tcagccatca tcagccgcaa ttttccgatc attggtgtga agagaagac    480
attcgagcag ctccacaaga agtgcctaga agaaaagtt ctttacctgg atcccgagtt    540
cccaccggat gagacctctc tcttttacag ccagaagttc cccatccagt tcgtctggaa    600
gagacctccg gaaatttgtg agaatccccg atttatcatt ggtggagcca acaggactga    660
catctgccaa ggagatctag gggactgctg gcttcttgca gccattgcct gtctgaccct    720
gaatgagcga ctgcttttcc gagttatacc tcatgatcaa gtttcactg aaaactacgc     780
agggatcttc cacttccagt tctggcgcta tggagactgg gtagatgtgg ttattgacga    840
```

-continued

```
ctgtctgccg acatacaaca accagctggt cttcaccaaa tccaaccacc gcaatgagtt    900
ctggagtgct ctactggaga aagcatatgc caagctccat ggttcctatg aagctctgaa    960
aggtgggaac accacagaag ccatggagga cttcacagga ggggtgacag agttttttga   1020
gatcaaggat gctccgagtg acatgtacaa gatcatgagg aaagctatcg agagaggctc   1080
cctcatgggc tgctccattg atgatggcac caacatgact tatggaacct ctccttctgg   1140
tctgaacatg ggggaattga ttgcgcggat ggtgagaaat atggataact cgctgctcag   1200
agactcagac ctggacccca gggcctcaga tgacagaccg tcacggacaa ttgttccggt   1260
gcagtatgaa acaagaatgg cctgtggact ggtgaaaggg cacgcctatt cagtcactgg   1320
gctggaggag cccctgttca aggcgagaa ggtgaagctg gtgcggctgc ggaacccctg    1380
ggccaggtg gagtggaacg gctcttggag tgatggttgg aaggactgga ctttgtgga    1440
caaagacgag aaggcccgtc tgcagcacca ggtcaccgag gatggagagt ctggatgtc    1500
atatgatgac tttgtctacc atttcacaaa gctggagatc tgcaacctca cagctgatgc   1560
cctggagtcc gataagcttc agacctggac agtgtctgta aatgagggcc gctgggtgag   1620
ggctgttct gctggaggct gccggaactt cccagacact ttctggacca cccgcagta    1680
ccgtctcaag ctcctggagg aggatgatga ccctgatgac tctgaggtga tttgcagctt   1740
cctcgtggct ctgatgcaga aaatcggcg caaggaccgg aagctggggg ccaacctctt   1800
caccattggc ttcgctatct acgaggttcc caaagagatg cacgggaata gcaacaccct   1860
gcagaaggac ttcttcttgt acaatgcctc caaggccagg agcaaaacct acatcaacat   1920
gcgggaggtg tcccagcgct ccgcctgcc gcccagcgag tatgtcattg tcccctccac   1980
ttacgagccc catcaggagg gggaattcat cctccgggtc ttctctgaaa agaggaatct   2040
ctctgaggaa gctgagaata caatctctgt ggaccggcca gtgaaaaaga aaaaaaacaa   2100
gcccatcatc ttcgtttcag acagagcaaa cagcaacaag gagctgggtg tggaccagga   2160
ggcagaggag ggcaaagaca aaacagggcc ggataaacaa ggggaaagcc cacagccacg   2220
gcctggccac acagaccagg agagtgagga gcagcagcaa ttccggaaca tcttcaggca   2280
gattgcaggc gacgacatgg agatctgtgc ggatgaactc aagaatgtcc ttaatacggt   2340
ggtgaacaaa cacaaggacc tgaagacaca agggttcact ctggagtcct gcagaagcat   2400
gatagctctc atggatacag atggctctgg gagactgaat cttcaagagt tccatcacct   2460
ctggaaaaag atcaaggcct ggcagaaaat cttcaaacac tatgacactg accattctgg   2520
taccatcaat agctatgaga tgcgaaatgc agtcaatgat gcaggcttcc atctcaacag   2580
ccaactctat gacatcatca ccatgcgcta cgcagacaaa cacatgaaca tcgactttga   2640
cagcttcatc tgctgcttcg tcaggctgga agggatgttc agagcttttc acgcatttga   2700
caaggatgga gatggcatca tcaaactgaa cgtacttgag tggctgcagc ttaccatgta   2760
tgcctgaacc agatgacctc atgtaagatc aaccaggatt ccatctcaac acgacacagc   2820
tagggctgtt taccacaagg aacccagtag gcacacctcc accaaactgg gctcctggtc   2880
acgttccttc tccactttga cccaagtctt ggtgcacagc cacctcaagt gtctggcttg   2940
ctgggagctc tgcagacgct gtctacatag cttgtaactg ggttgtccac agccctgtca   3000
ccatctgcac tcagttctgc cagttttagg gtgggtctac tctgggtcc ataggggtgtg   3060
gataacctgac aaaaatgtgg ctacacttct gaaagaatct atctaaataa aggcacgcac   3120
atggctggtt ccaccatt                                                  3138
```